United States Patent
Nelson et al.

(10) Patent No.: US 6,818,634 B2
(45) Date of Patent: Nov. 16, 2004

(54) 7-AND 9-CARBAMATE, UREA, THIOUREA, THIOCARBAMATE, AND HETEROARYL-AMINO SUBSTITUTED TETRACYCLINE COMPOUNDS

(75) Inventors: Mark L. Nelson, Wellesley, MA (US); Stuart B. Levy, Boston, MA (US); Roger Frechette, Reading, MA (US); Todd E. Bowser, Charlton, MA (US); Mohamed Y. Ismail, Bedford, MA (US)

(73) Assignees: Paratek Pharmaceuticals, Inc., Boston, MA (US); Trustees of Tufts College, Medford, MA (US)

(*) Notice: Subject to any disclaimer, the term of this patent is extended or adjusted under 35 U.S.C. 154(b) by 0 days.

(21) Appl. No.: 09/823,884

(22) Filed: Mar. 30, 2001

(65) Prior Publication Data

US 2002/0103171 A1 Aug. 1, 2002

Related U.S. Application Data

(60) Provisional application No. 60/280,367, filed on Mar. 29, 2001, provisional application No. 60/193,972, filed on Mar. 31, 2000, and provisional application No. 60/193,879, filed on Mar. 31, 2000.

(51) Int. Cl.[7] .................. A61K 31/65; C07D 277/42
(52) U.S. Cl. .................................. 514/152; 548/194
(58) Field of Search ..................... 548/194; 514/152

(56) References Cited

U.S. PATENT DOCUMENTS

| | | | |
|---|---|---|---|
| 2,980,584 A | 4/1961 | Hammer | 167/65 |
| 2,990,331 A | 6/1961 | Neumann et al. | 167/65 |
| 3,062,717 A | 11/1962 | Hammer | 167/65 |
| 3,165,531 A | 1/1965 | Blackwood et al. | 260/330.5 |
| 3,338,963 A | 8/1967 | Petisi et al. | 260/559 |
| 3,454,697 A | 7/1969 | Joyner et al. | 424/227 |
| 3,483,251 A | 12/1969 | Zarbrano | 260/559 |
| 3,557,280 A | 1/1971 | Weber et al. | 424/80 |
| 3,674,859 A | 7/1972 | Beutel et al. | 424/80 |
| 3,957,980 A | 5/1976 | Noseworthy | 424/227 |
| 4,018,889 A | 4/1977 | Armstrong | 424/80 |
| 4,024,272 A | 5/1977 | Rogalski et al. | 424/275 |
| 4,126,680 A | 11/1978 | Armstrong | 424/80 |
| 5,401,729 A | 3/1995 | Sum et al. | 514/152 |
| 5,532,227 A | 7/1996 | Golub et al. | 514/152 |
| 5,789,395 A | 8/1998 | Amin et al. | 514/152 |
| 5,834,450 A | 11/1998 | Su | 514/152 |

FOREIGN PATENT DOCUMENTS

| | | |
|---|---|---|
| EP | 536 515 A1 | 4/1993 |
| WO | WO 94/15587 A2 | 7/1994 |
| WO | WO 99/37306 A1 | 7/1999 |

OTHER PUBLICATIONS

Albar HA, et al., Synthesis of Novel Spiro and Fused Cyclopenta(c)–pyrazole and –Pyrimidine Derivatives, J. Chem. Research. 1997:40–41.

Barden TC. et al. "Glycylcyclines", 3.9–Aminodoxycyclinecarboxamides. J Med Chem. Sep. 30, 1994; 37(20):3205–11.

Berge SM, et al. Pharmaceutical salts, J. Pharm Sci. Jan. 1977, 66(1):1–19.

Beyer L, et al. Synthesis and Characterization of Thiourea Derivatives of '–Aminoacids. Crystal Structure of Methyl L–valinate and L–leucinate Derivatives. Tetrahedron 1996;52(17):6233–6240.

Fikry RM, Synthesis of some New Pyrimidine and Condensed Pyrimidine Derivatives. J. Indian. Chem. Soc. Dec. 1996;73:698–699.

Kassem EM, et al. Synthesis of New Benzothiazole–2–Acrylic Acid Derivatives. Pak. J. Sci. Ind. Res. Dec. 1995;38(11–12):424–427.

Nassar SA, et al. Synthesis and Characterization of Some Biologically Active Pyrimidine Derivatives Containing Sulphur. 1997;40(3):239–247.

*Primary Examiner*—Robert Gerstl
(74) *Attorney, Agent, or Firm*—Lahive & Cockfield, LLP; Elizabeth A. Hanley, Esq.; Cynthia M. Soroos, Esq.

(57) ABSTRACT

Substituted tetracycline compounds, methods of synthesis, and methods of use are discussed. Tetracyclines useful for treating tetracycline related disorders are also discussed. Intermediates useful for synthesizing other tetracycline compounds are also included.

81 Claims, No Drawings

7-AND 9-CARBAMATE, UREA, THIOUREA, THIOCARBAMATE, AND HETEROARYL-AMINO SUBSTITUTED TETRACYCLINE COMPOUNDS

RELATED APPLICATIONS

This application claims priority to U.S. Provisional Application No. 60/280,367, filed Mar. 29, 2001, entitled "7- and 9-Carbamate, Urea, Thiourea, Thiocarbamate, and Heteroaryl-Amino Substituted Tetracycline Compounds;" U.S. Provisional Application No. 60/193,972, filed Mar. 31, 2000, entitled "Methods for Synthesizing 7- or 9-Substituted Tetracycline Compounds and Reactive Intermediates;" and to U.S. Provisional Application No. 60/193,879, filed Mar. 31, 2000, entitled "9-Substituted Tetracycline Compounds." The entire contents of all of the aforementioned applications are hereby incorporated herein by reference.

BACKGROUND OF THE INVENTION

The development of the tetracycline antibiotics was the direct result of a systematic screening of soil specimens collected from many parts of the world for evidence of microorganisms capable of producing bacteriocidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of tetracycline compounds, without the ring-attached methyl group present in earlier tetracyclines, was prepared in 1957 and became publicly available in 1967.

Recently, research efforts have focused on developing new tetracycline antibiotic compositions effective under varying therapeutic conditions and routes of administration. New tetracycline analogues have also been investigated which may prove to be equal to or more effective than the originally introduced tetracycline compounds. Examples include U.S. Pat. Nos. 3,957,980; 3,674,859; 2,980,584; 2,990,331; 3,062,717; 3,557,280; 4,018,889; 4,024,272; 4,126,680; 3,454,697; and 3,165,531. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., pneumococci and Salmonella). The rise of tetracycline-resistant organisms has resulted in a general decline in use of tetracyclines and tetracycline analogue compositions as antibiotics of choice.

SUMMARY OF THE INVENTION

The invention pertains, at least in part, to substituted tetracycline compounds of the formula (I):

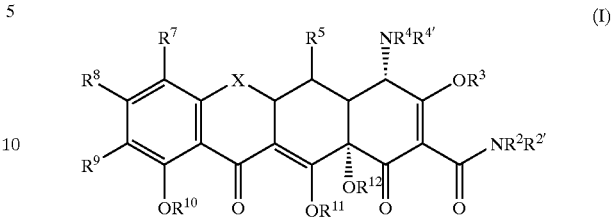

wherein:
X is $CHC(R^{13}Y'Y)$, $CR^{6'}R^{6}$, S, $NR^{6}$, or O;
$R^{2}$ is hydrogen, alkyl, alkynyl, alkoxy, alkylthio, alkylsulfinyl, alkylsulfonyl, alkylamino, arylalkyl, aryl, heterocyclic, heteroaromatic or a prodrug moiety;
$R^{4}$ and $R^{4'}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^{2'}$, $R^{3}$, $R^{10}$, $R^{11}$ and $R^{12}$ are each hydrogen or a pro-drug moiety;
$R^{5}$ is hydrogen, hydroxyl, or a prodrug moiety;
$R^{6}$, $R^{6'}$, and $R^{8}$ are each independently hydrogen, alkyl, alkenyl, alkynyl, aryl, alkoxy, alkylthio, alkylsulfinyl, alkylsulfonyl, alkylamino, arylalkyl, or halogen;
$R^{7}$ is hydrogen, dialkylamino, heteroaryl-amino, or $NR^{7c}C(=W')WR^{7a}$;
$R^{13}$ is hydrogen, hydroxy, alkyl; alkenyl; alkynyl; alkoxy; alkylthio; alkylsulfinyl; alkylsulfonyl; alkylamino; or an arylalkyl;
Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or arylalkyl;
$R^{9}$ is hydrogen, heteroaryl-amino, or $NR^{9c}C(=Z')ZR^{9a}$;
Z is $CR^{9d}R^{9e}$, $NR^{9b}$, or O;
Z' is O or S;
$R^{9a}$, $R^{9b}$, $R^{9c}$, $R^{9d}$, and $R^{9e}$ are each independently hydrogen, alkyl, alkenyl, alkynyl, alkoxy, alkylthio, alkylsulfinyl, alkylsulfonyl, arylsulfonyl, alkoxycarbonyl, arylcarbonyl, alkylamino, arylalkyl, aryl, heterocyclic, heteroaromatic, absent, or a prodrug moiety, and $R^{9d}$ and $R^{9e}$ may be linked to form a ring;
W is $CR^{7d}R^{7e}$, $NR^{7b}$ or O;
W' is O or S; and
$R^{7a}$, $R^{7b}$, $R^{7c}$, $R^{7d}$, and $R^{7e}$ are each independently hydrogen, alkyl, alkenyl, alkynyl, alkoxy, alkylthio, alkylsulfinyl, arylsulfonyl, alkoxycarbonyl, arylcarbonyl, alkylamino, arylalkyl, aryl, heterocyclic, heteroaromatic, absent, or a prodrug moiety, and $R^{7d}$ and $R^{7e}$ may be linked to form a ring;
and pharmaceutically acceptable salts thereof, provided that $R^{9}$ is not hydrogen when $R^{7}$ is dialkylamino or hydrogen.

The invention also pertains, at least in part, to methods for treating a tetracycline responsive state in a subject. The method includes administering to the subject a substituted tetracycline compound of formula (I).

In another embodiment, the invention includes pharmaceutical compositions comprising a therapeutically effective amount of a substituted tetracycline compound of formula (I) and a pharmaceutically acceptable carrier.

In yet another embodiment, the invention pertains to a method for synthesizing 7- and/or 9-substituted tetracycline compounds. The method includes contacting a tetracycline compound with a nitrating agent, under conditions such that a nitro tetracycline compound is formed, contacting the nitro tetracycline compound with a hydrogenating agent, under conditions such that an amino tetracycline compound is formed, and contacting the amino tetracycline compound with an amino reactive substrate, such that a 9- or 7-substituted tetracycline compound is formed.

The invention also pertains, at least in part, to a method for synthesizing a 7- and/or 9-substituted tetracycline compound of formula (I), by contacting a reactive intermediate with appropriate reagents under appropriate conditions, such that a substituted tetracycline compound of formula (I) is formed.

The reactive intermediate, wherein said reactive intermediate is of the formula:

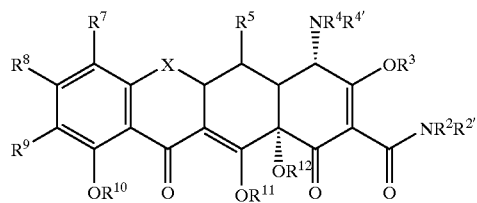

wherein:

X is $CHC(R^{13}Y'Y)$, $CHR^6$, S, $NR^6$, or O;

$R^2$ is hydrogen, alkyl, alkynyl, alkoxy, alkylthio, alkylsulfinyl, alkylsulfonyl, alkylamino, arylalkyl, aryl, heterocyclic, heteroaromatic or a prodrug moiety;

$R^4$ and $R^{4'}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{2'}$, $R^3$, $R^{10}$, $R^{11}$ and $R^{12}$ are each hydrogen or a pro-drug moiety;

$R^5$ is hydrogen, hydroxyl, or a prodrug moiety;

$R^6$ and $R^8$ are each independently hydrogen, alkyl, alkenyl, alkynyl, aryl, alkoxy, alkylthio, alkylsulfinyl, alkylsulfonyl, alkylamino, or an arylalkyl;

$R^{13}$ is hydrogen, hydroxy, alkyl; alkenyl; alkynyl; alkoxy; alkylthio; alkylsulfinyl; alkylsulfonyl; alkylamino; or an arylalkyl;

Y' and Y are each independently hydrogen; halogen; hydroxyl; cyano, sulfhydryl; amino; alkyl; alkenyl; alkynyl; alkoxy; alkylthio; alkylsulfinyl; alkylsulfonyl; alkylamino; or an arylalkyl;

$R^7$ is hydrogen, dialkylamino, thiourea, diazonium salt, thiocarboxamide, or nitro;

$R^9$ is hydrogen, thiourea, diazonium salt, thiocarboxamide, or nitro; and pharmaceutically acceptable salts thereof, provided that $R^9$ is not hydrogen when $R^7$ is hydrogen or dialkylamino.

DETAILED DESCRIPTION OF THE INVENTION

The present invention pertains, at least in part, to novel 7- and 9-substituted tetracycline urea, thiourea, carbamate, thiocarbamate, amino-thiazolyl, and amino-heteroaryl compounds. These compounds can be used to treat numerous tetracycline compound-responsive states, such as bacterial infections and neoplasms, as well as other known applications for tetracycline compounds, such as tetracycline efflux blockers and gene expression modulation.

In one embodiment, the invention includes 7- and 9-substituted tetracycline compounds. Preferably, the substituted tetracycline compounds are of formula (I):

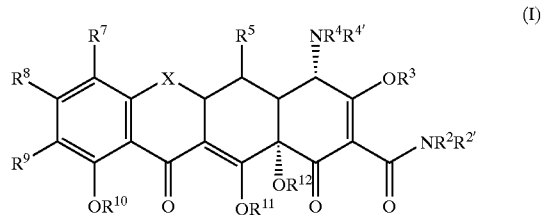

wherein:

X is $CHC(R^{13}Y'Y)$, $CR^{6'}R^6$, S, $NR^6$, or O;

$R^2$ is hydrogen, alkyl alkynyl, alkoxy, alkylthio, alkylsulfinyl, alkylsulfonyl, alkylamino, arylalkyl, aryl, heterocyclic, heteroaromatic or a prodrug moiety;

$R^4$ and $R^{4'}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{2'}$, $R^3$, $R^{10}$, $R^{11}$ and $R^{12}$ are each hydrogen or a pro-drug moiety;

$R^5$ is hydrogen, hydroxyl, or a prodrug moiety;

$R^6$, $R^{6'}$, and $R^8$ are each independently hydrogen, alkyl, alkenyl, alkynyl, aryl, alkoxy, alkylthio, alkylsulfinyl, alkylsulfonyl, alkylamino, arylalkyl, or halogen;

$R^7$ is hydrogen, dialkylamino, heteroaryl-amino, or $NR^{7c}C(=W')WR^{7a}$;

$R^{13}$ is hydrogen, hydroxy, alkyl; alkenyl; alkynyl; alkoxy; alkylthio; alkylsulfinyl; alkylsulfonyl; alkylamino; or an arylalkyl;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or arylalkyl;

$R^9$ is hydrogen, heteroaryl-amino, or $NR^{9c}C(=Z')ZR^{9a}$;

Z is $CR^{9d}R^{9e}$, $NR^{9b}$, or O;

Z' is O or S;

$R^{9a}$, $R^{9b}$, $R^{9c}$, $R^{9d}$, and $R^{9e}$ are each independently hydrogen, alkyl, alkenyl, alkynyl, alkoxy, alkylthio, alkylsulfinyl, alkylsulfonyl, arylsulfonyl, alkoxycarbonyl, arylcarbonyl, alkylamino, arylalkyl, aryl, heterocyclic, heteroaromatic, absent, or a prodrug moiety, and $R^{9d}$ and $R^{9e}$ may be linked to form a ring;

W is $CR^{7d}R^{7e}$, $NR^{7b}$ or O;

W' is O or S; and $R^{7a}$, $R^{7b}$, $R^{7c}$, $R^{7d}$, and $R^{7e}$ are each independently hydrogen, alkyl, alkenyl, alkynyl, alkoxy, alkylthio, alkylsulfinyl, arylsulfonyl, alkoxycarbonyl, arylcarbonyl, alkylamino, arylalkyl, aryl, heterocyclic, heteroaromatic, absent, or a prodrug moiety, and $R^{7d}$ and $R^{7e}$ may be linked to form a ring, and pharmaceutically acceptable salts thereof, provided that $R^9$ is not hydrogen when $R^7$ is dialkylamino or hydrogen.

The term "tetracycline compound" includes many compounds with a similar ring structure to tetracycline. Examples of tetracycline compounds include: tetracycline, chlortetracycline, oxytetracycline, demeclocycline, methacycline, sancycline, doxycycline, and minocycline. Other derivatives and analogues comprising a similar four ring structure are also included. Table 1 depicts tetracycline and several known tetracycline derivatives. In an embodiment, the term "unsubstituted tetracycline compounds," includes tetracycline compounds wherein $R^7$ is not $NR^{7c}C(=W')WR^{7a}$ nor heteroaryl-amino and wherein $R^9$ is not heteroaryl-amino nor $NR^{9c}C(=Z')ZR^{9a}$.

TABLE I

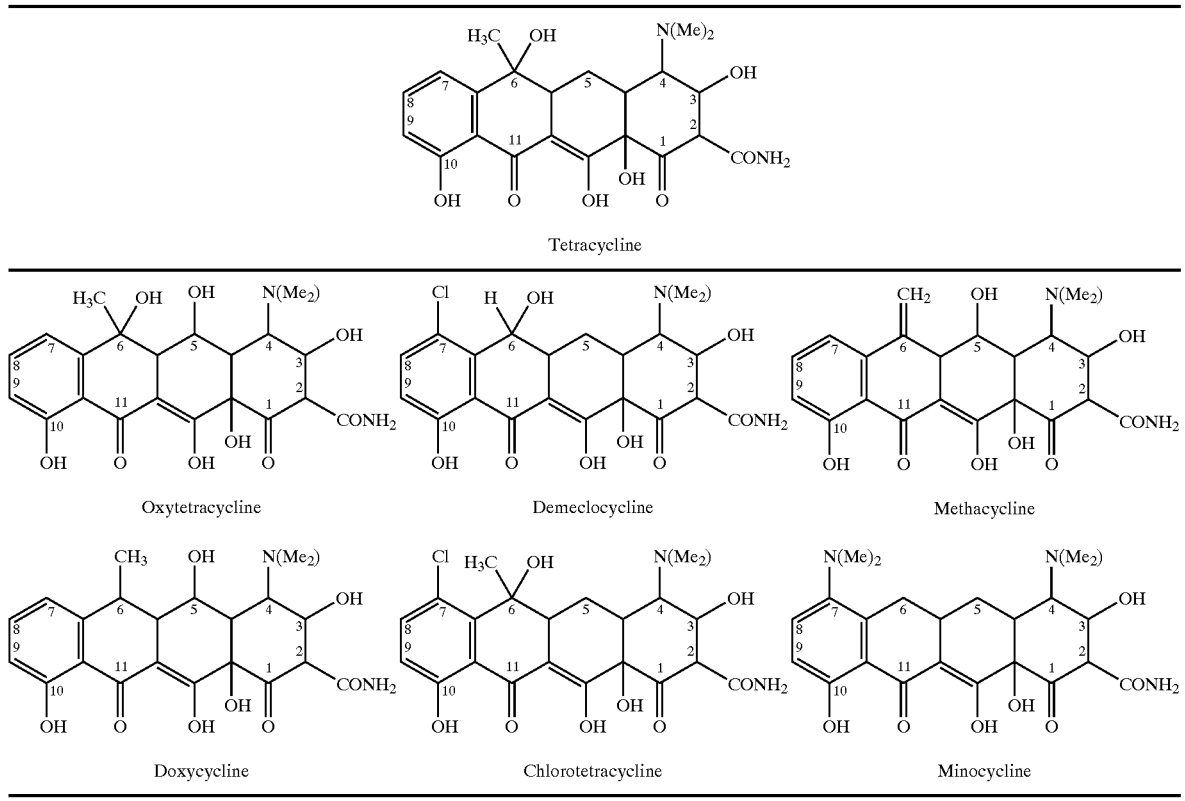

The term "substituted tetracycline compounds" includes tetracycline compounds with substitution at the 7- or 9-position. In one embodiment, the substitution at the 7- or 9-position enhances the ability of the substituted tetracycline compound to perform its intended function. In an embodiment, the 9-substituted tetracycline compound is 9-substituted minocycline (e.g., wherein $R^4$ and $R^{4'}$ are methyl, $R^5$ is hydrogen, $R^7$ is dimethyl amino, and X is $CR^6R^{6'}$, wherein both $R^6$ and $R^{6'}$ are hydrogen atoms); 7- or 9-substituted doxycycline (e.g., wherein $R^4$ and $R^{4'}$ are methyl, $R^5$ is hydroxyl, X is $CR^6R^{6'}$, $R^6$ is methyl and $R^{6'}$ is hydrogen); or a 7- or 9-substituted sancycline (wherein $R^4$ and $R^{4'}$ are methyl; $R^5$ is hydrogen, X is $CR^6R^{6'}$, $R^6$ and $R^{6'}$ are hydrogen atoms). In a further embodiment, $R^5$ may be a protected hydroxyl group, e.g., a prodrug moiety. Examples of prodrug moieties include, for example, acyl esters and propionoic acid esters. In certain embodiments, the prodrug moiety is aroyl, alkanoyl, or alkaroyl and may or may not be cleaved in vivo to the hydroxyl group. In an embodiment, $R^{2'}$, $R^3$, $R^8$, $R^{10}$, $R^{11}$, and $R^{12}$ are each hydrogen. In certain embodiments of the invention, the term substituted tetracycline compounds includes tetracycline compounds wherein least one of $R^7$ or $R^9$ is heteroaryl-amino, $NR^{7c}C(=W')WR^{7a}$, or $NR^{9c}C(=Z')ZR^{9a}$.

The term "9-substituted tetracycline compounds" includes, in one embodiment, compounds wherein $R^9$ is amino-heteroaryl or $NR^{9c}C(=Z')ZR^{9a}$. In a further embodiment, $R^{9c}$ is hydrogen. In another, Z' is oxygen or sulfur. In an embodiment, Z is oxygen or $NR^{9b}$, wherein $R^{9b}$ is hydrogen. In another further embodiment, $R^{9a}$ may be hydrophobic. $R^{9a}$ may also be alkyl, alkenyl (e.g., ethenyl, propenyl, butenyl, etc.), alkynyl, aryl(e.g., phenyl, heteroaryl, etc.), arylalkyl, or multicyclic (e.g., polycyclic, e.g., steroidyl, e.g., chlolesteroidyl).

In one embodiment, $R^{9a}$ is substituted or unsubstituted alkyl (e.g., methyl, ethyl, t-butyl, n-butyl, i-butyl, or n-pentyl.) Examples of possible substituents include but are not limited to, alkyl, alkenyl, halogen, hydroxyl, alkoxy, alkylcarbonyloxy, alkyloxycarbonyl, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl. In certain embodiments, the substituents are alkoxycarbonyl, amino, arylcarbonyl, halogen, hydroxy, alkylamino, alkoxy, or aryl. In certain embodiments, the substituent is halogen (e.g., bromine, chlorine, iodine, fluorine).

In a further embodiment, $R^{9a}$ includes at least one aryl group, e.g., heteroaryl, phenyl, naphthyl, fluorene, etc. Fluorene is a moiety of the formula:

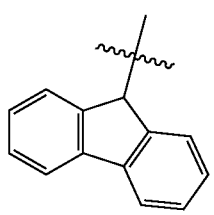

In one embodiment, $R^{9a}$ is aryl, e.g., substituted or unsubstituted phenyl. Examples of substituents include, but are not limited to, alkyl (e.g., unsubstituted, e.g., methyl, ethyl, propyl, butyl, or substituted, e.g., chloromethyl, dichloromethyl, perchloromethyl, fluoromethyl, difluoromethyl, perfluoromethyl, etc.), alkenyl, alkynyl, aryl, alkoxy (e.g., methoxy, ethoxy, propoxy, etc.), aryloxy, alkylcarbonyl, arylcarbonyl, alkoxycarbonyl, aryloxycarbonyl, amido, halogen, nitro, azo, alkyl sulfonyl, and arylsulfonyl.

In another embodiment, $R^9$ is amino-heteroaryl (e.g., —NH-heteroaryl, e.g., amino-thioazolyl). The thioazolyl substituent may be substituted with substituents such as phenyl rings. Scheme 3 below shows some representative substituents of the thioazole ring. For example, in one embodiment, the thiazole can be substituted with a phenyl group, a biphenyl group, an adamantyl group, etc. The substituents of the thiazole can also be further substituted, e.g., with an electron donating group, or an electron withdrawing group. Examples of electron withdrawing substituents include aryl groups (e.g., phenyl), halogens (e.g., chlorine, bromine, or fluorine), alkoxy groups (e.g., methoxy, ethoxy), amines (e.g., secondary amines, such as, diethylamine, dimethylamine unsubstituted amines, etc.), nitro groups, etc. In other embodiments, the thiazolyl ring is linked to the tetracycline compound through an ether (—O—), alkyl, or other linkage which allows the substituted tetracycline compound to perform its intended function.

For example, in one embodiment, $R^9$ is substituted or unsubstituted heteroaryl-amino, e.g., thiazolyl amino. Examples of substituents of the heteroaryl include, but are not limited to, alkyl, alkenyl, halogen, hydroxyl, alkoxy, alkylcarbonyloxy, alkyloxycarbonyl, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulflhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In certain embodiments, the substituents of the thiazolyl include alkyl (e.g., methyl, ethyl, propyl, butyl, etc.), halogen (e.g., fluorine, bromine, chlorine, iodine, etc.), alkoxy (e.g., methoxy, propoxy, ethoxy, etc.), aryl (e.g., substituted or unsubstituted phenyl or heteroaryl).

In an embodiment, the aryl thiazolyl substituent is substituted with one or more substituents. Examples of substituents include, but are not limited to, alkyl (e.g., methyl, ethyl, propyl, butyl, etc.), alkenyl, alkynyl, aryl, alkoxy, aryloxy, alkylcarbonyl, arylcarbonyl, amido, trifluoromethyl, halogen, nitro, azo, alkyl sulfonyl, alkoxycarbonyl (e.g., methoxycarbonyl, ethoxycarbonyl, etc.), aryloxycarbonyl, and arylsulfonyl.

The term "7-substituted tetracycline compounds" includes tetracycline compounds with substitution at the 7 position. Examples of tetracycline compounds which advantageously may be substituted at the 7 position include tetracycline, sancycline, doxycycline, oxytetracycline, demeclocycline, or methacycline. In an advantageous embodiment, $R^7$ is $NR^{7c}C(=W')WR^{7a}$, wherein $R^{7c}$ may be hydrogen, W' may be oxygen or sulfur. $R^{7a}$ may be hydrophobic. $R^{7a}$ may also be alkyl, alkenyl (e.g., ethenyl, propenyl, butenyl, etc.), alkynyl, aryl (e.g., phenyl, heteroaryl, etc.), arylalkyl, heteroaromatic, or multicyclic (e.g., polycyclic, e.g., steroidyl, e.g., chlolesteroidyl). $R^{7a}$ may also include at least one phenyl group, e.g., naphthyl or fluorene. In a preferred embodiment, W is oxygen or $NR^{7b}$, wherein $R^{7b}$ is hydrogen.

In one embodiment, $R^{7a}$ is substituted or unsubstituted alkyl (e.g., methyl, ethyl, t-butyl, n-butyl, i-butyl, or n-pentyl.) Examples of possible substituents include but are not limited to, alkyl, alkenyl, halogen, hydroxyl, alkoxy, alkylcarbonyloxy, alkyloxycarbonyl, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfbydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl. In certain embodiments, the substituents are alkoxycarbonyl, amino, arylcarbonyl, halogen, hydroxy, alkylamino, alkoxy, or aryl. In certain embodiments, the substituent is halogen (e.g., bromine, chlorine, iodine, fluorine). In a further embodiment, $R^{7a}$ includes at least one aryl group, e.g., heteroaryl, phenyl, naphthyl, fluorene, etc.

In one embodiment, $R^{7a}$ is aryl, e.g., substituted or unsubstituted phenyl. Examples of substituents include, but are not limited to, alkyl (e.g, unsubstituted, e.g., methyl, ethyl, propyl, butyl, or substituted, e.g., chloromethyl, dichloromethyl, perchloromethyl, fluoromethyl, difluoromethyl, perfluoromethyl, etc.), alkenyl, alkynyl, aryl, alkoxy (e.g., methoxy, ethoxy, propoxy, etc.), aryloxy, alkylcarbonyl, arylcarbonyl, alkoxycarbonyl, aryloxycarbonyl, amido, halogen, nitro, azo, alkyl sulfonyl, and arylsulfonyl.

In another embodiment, $R^7$ is amino-heteroaryl (e.g., —NH-heteroaryl, e.g., amino-thioazolyl). The thioazolyl substituent may be substituted with substituents such as phenyl rings. Scheme 3 below shows some representative substituents of the thioazole ring. For example, in one embodiment, the thiazole can be substituted with a phenyl group, a biphenyl group, an adamantyl group, etc. The substituents of the thiazole can also be further substituted, e.g., with an electron donating group, or an electron withdrawing group. Examples of electron withdrawing substituents include aryl groups (e.g., phenyl), halogens (e.g., chlorine, bromine, or fluorine), alkoxy groups (e.g., methoxy, ethoxy), amines (e.g., secondary amines, such as, diethylamine, dimethylamine unsubstituted amines, etc.), nitro groups, etc. In other embodiments, the thiazolyl ring is linked to the tetracycline compound through an ether (—O—), alkyl, or other linkage which allows the substituted tetracycline compound to perform its intended function.

For example, in one embodiment, $R^7$ is substituted or unsubstituted heteroaryl-amino, e.g., thiazolyl amino.

Examples of substituents of the heteroaryl include, but are not limited to, alkyl, alkenyl, halogen, hydroxyl, alkoxy, alkylcarbonyloxy, alkyloxycarbonyl, arylcarbonyloxy, alkoxycarbonylamino, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, aminoalkyl, arylalkylcarbonyl, alkenylcarbonyl, alkoxycarbonyl, silyl, aminocarbonyl, alkylthiocarbonyl, phosphate, aralkyl, phosphonato, phosphinato, cyano, amino, acylamino, amido, imino, sulfhydryl, alkylthio, sulfate, arylthio, thiocarboxylate, alkylsulfinyl, sulfonato, sulfamoyl, sulfonamido, nitro, cyano, azido, heterocyclyl, alkylaryl, aryl and heteroaryl.

In certain embodiments, the substituents of the thiazolyl include alkyl (e.g., methyl, ethyl, propyl, butyl, etc.), halogen (e.g., fluorine, bromine, chlorine, iodine, etc.), alkoxy (e.g., methoxy, propoxy, ethoxy, etc.), aryl (e.g., substituted or unsubstituted phenyl or heteroaryl).

In an embodiment, the aryl thiazolyl substituent is substituted with one or more substituents. Examples of substituents include, but are not limited to, alkyl (e.g., methyl, ethyl, propyl, butyl, etc.), alkenyl, alkynyl, aryl, alkoxy, aryloxy, alkylcarbonyl, arylcarbonyl, amido, trifluoromethyl, halogen, nitro, azo, alkyl sulfonyl, alkoxycarbonyl (e.g., methoxycarbonyl, ethoxycarbonyl, etc.), aryloxycarbonyl, and arylsulfonyl.

In a further embodiment of the invention, $R^{2'}$, $R^3$, $R^{10}$, $R^{11}$, and $R^{12}$ of the substituted tetracycline compounds are each hydrogen atoms. In another further embodiment, $R^4$ and $R^{4'}$ are each alkyl, e.g., lower alkyl, and, advantageously, methyl. In another embodiment, X is $CR^6R^{6'}$, $R^6$ and $R^{6'}$ are selected from the group consisting of hydrogen, methyl, and hydroxy groups.

In another embodiment, the invention also pertains to compounds wherein both $R^9$ and $R^7$ are not hydrogen. These compounds may be referred to as 7- and 9-disubstituted compounds. The invention pertains to compounds with any combination of 7- and 9-substituents disclosed herein.

Examples of compounds of the invention include those disclosed in Table 2, in addition to the compounds listed below. The invention also pertains to pharmaceutically acceptable salts of any of these compounds as well as enantiomers, and mixtures of the compounds. Examples of compounds of the invention include, but are not limited to:

Doxycycline 9-carbamic acid 9H-fluoren-9-ylmethyl ester;
(9-(Naphthyn-1-yl) doxycycline urea;
9-(3-Methyl-1-butyl) doxycycline urea;
9-Phenyl doxycycline urea;
9-t-Butyl doxycycline urea;
FMOC 9-amino doxycycline;
9-(4'-Chloro-2'-trifluoromethylphenyl) doxycycline urea;
9-(4'-Fluorophenyl) doxycycline carbamate;
9-(4'-Methoxyphenyl) doxycycline carbamate;
9-BOC amino doxycycline;
9-(Phenylthiazolyl) amino doxycycline;
9-(Ethylthiazolyl) amino doxycycline;
(4-Fluorophenylthiazolyl) amino doxycycline;
9-(4'-Methoxyphenylthiazolyl) amino doxycycline;
9-(3'-Nitrophenylthiazolyl) amino doxycycline;
9-(4'-Methyl, 5'-phenylthiazolyl) amino doxycycline;
9-Neopentyl minocycline carbamate;
9-(Phenylthiazolyl) amino sancycline;
9-(Adamantylthiazolyl) amino doxycycline;
9-(Naphthyn-1-yl urea) Doxycycline 5-propanoic acid ester;
Doxycycline 9-Thiocarbamic acid 9H-fluoren-9-ylmethyl ester;
(9-(Naphthyn-1-yl) doxycycline thiourea;
9-(3-methyl-1-butyl) doxycycline thiourea;
9-Phenyl doxycycline thiourea;
9-t-Butyl doxycycline thiourea;
9-(4'-Chloro-2'-trifluoromethylphenyl) doxycycline thiourea;
9-(4'-Fluorophenyl) doxycycline thiocarbamate;
9-(4'-Methoxyphenyl) doxycycline thiocarbamate;
9-Neopentyl minocycline thiocarbamate;
9-(Naphthyn-1-yl) doxycycline thiourea 5-propanoic acid ester;
Minocycline 9-carbamic acid 9H-fluoren-9-ylmethyl ester;
(9-(Naphthyn-1-yl) minocycline urea;
9-(3-Methyl-1-butyl) minocycline urea;
9-Phenyl doxycycline urea;
9-t-Butyl minocycline urea;
FMOC 9-amino minocycline;
9-(4'-Chloro-2'-trifluoromethylphenyl) minocycline urea;
9-(4'-Fluorophenyl) minocycline carbamate;
9-(4'-Methoxyphenyl) minocycline carbamate;
9-BOC amino minocycline;
9-(Phenylthiazolyl) amino minocycline;
9-(Ethylthiazolyl) amino minocycline;
(4'-Fluorophenythiazolyl) amino minocycline;
9-(4'-Methoxyphenylthiazolyl) amino minocycline;
9-9-(3'-Nitrophenylthiazolyl) amino minocycline;
9-(4'-Methyl, 5'-phenylthiazolyl) amino doxycycline;
9-Neopentyl doxycycline carbamate;
9-(Phenylthiazolyl) amino minocycline;
9-(Adamantylthiazolyl) amino minocycline;
Minocycline 9-thiocarbamic acid 9H-fluoren-9-ylmethyl ester;
(9-(Naphthyn-1-yl) minocycline thiourea;
9-(3'-Methyl-1-butyl) minocycline thiourea;
9-Phenyl minocycline thiourea;
9-t-Butyl minocycline thiourea;
9-(4'-Fluorophenyl) minocycline thiocarbamate;
9-(4'-Methoxyphenyl) minocycline thiocarbamate;
9-Neopentyl doxycycline thiocarbamate;
9-(2'-Bromoethyl) doxycycline carbamate;
9-(n-Pentyl) minocycline carbamate;
9-(4'-Benzoylbenzoyl) amino doxycycline;
7-(3'-Nitrophenylthiazolyl) amino sancycline;
9-(3'-Ethoxycarbonylthiazolyl) amino doxycycline;
7-(4'-Methylphenyl) sancycline carbamate;
9-(4'-Trifluoromethoxyphenyl) minocycline urea;
9-(3',5'-diperfluorophenyl) minocycline thiourea;
9-Prop-2'-enyl minocycline carbamate;
9-(4'-Chloro, 2'-nitrophenyl) minocycline urea;
9-Ethyl minocycline carbamate;
9-n-Butyl minocycline carbamate;
9-n-But-3-enyl minocycline carbamate;
Doxycycline 7-carbamic acid 7H-fluoren-7-ylmethyl ester;
7-(Naphthyn-1-yl) doxycycline urea;
7-(3-Methyl-1-butyl) doxycycline urea;
7-Phenyl doxycycline urea;
7-t-Butyl doxycycline urea;
7-Fmoc amino doxycycline;
7-(4'-Chloro-2-trifluoromethylphenyl) doxycycline urea;
7-(4'-Fluorophenyl) doxycycline carbamate;
7-(4'-Methoxyphenyl) doxycycline carbamate;
7-BOC amino doxycycline;
7-(3'Phenylthiazolyl) amino doxycycline;

7-(3'-Ethylthiazolyl) amino doxycycline;
7-(4"-Fluorophenylthiazolyl) amino doxycycline;
7-(4"-Methoxyphenylthiazolyl) amino doxycycline;
7-(Phenylthiazolylamino)-sancycline;
7-(3'-Nitrophenylthiazolyl) amino doxycycline;
7-(4'-Methyl, 5'-phenylthiazolyl) amino doxycycline;
7-(Adamantylthiazolyl) amino doxycycline;
Doxycycline 7-thiocarbamic acid 7H-fluoren-7-ylmethyl ester;
7-(Naphthyn-1-yl) doxycycline thiourea;
7-(3-Methyl-1-butyl) doxycycline thiourea;
7-Phenyl amino doxycycline thiourea;
7-t-butyl amino doxycycline thiourea;
7-(4'-Chloro-2'-trifluoromethylphenyl) doxycycline thiourea;
7-(4'-Fluorophenyl) doxycycline thiocarbamate;
7-(4'-Methoxyphenyl) doxycycline thiocarbamate;
7-(Naphthyn-1-yl) doxycycline urea 5-propanoic acid ester;
9-i-Butyl minocycline carbamate,
7-(Naphthyn-1-yl) doxycycline thiourea 5-propanoic acid ester, and pharmaceutically acceptable salts thereof.

Other compounds of the invention include compounds having the following structures:

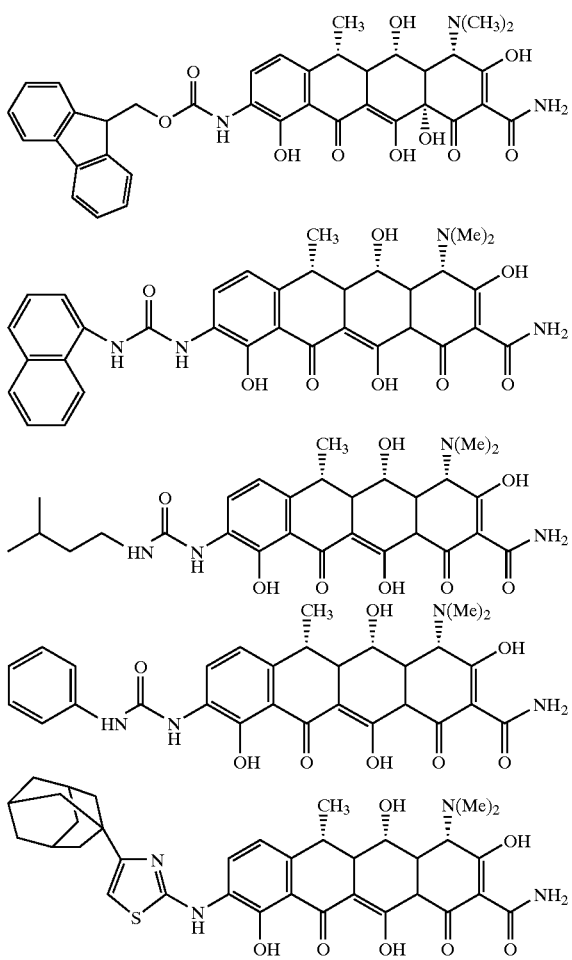

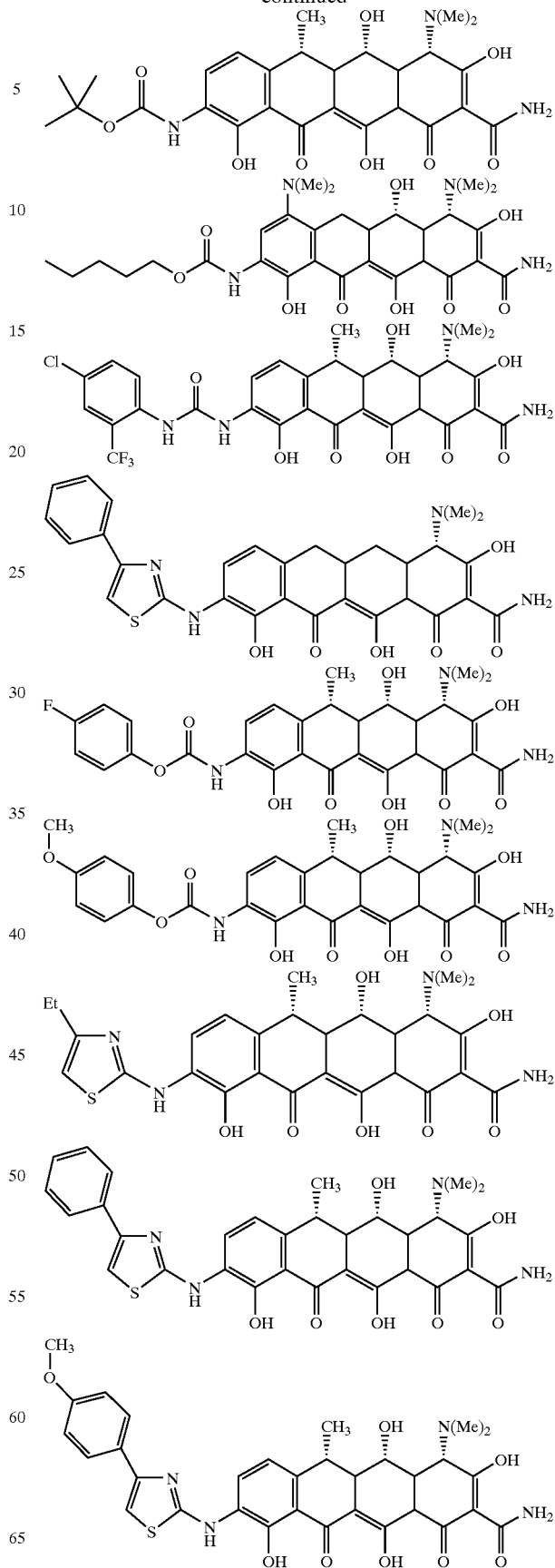

-continued
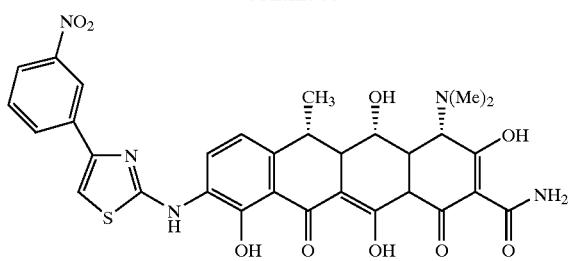
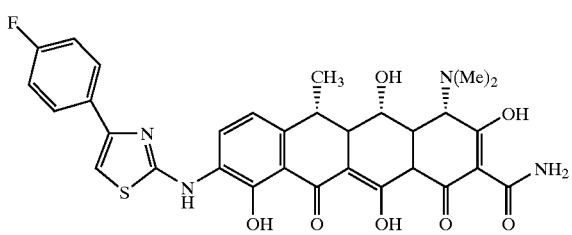
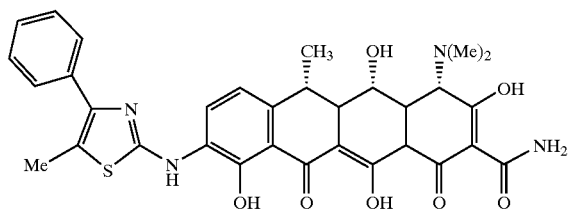
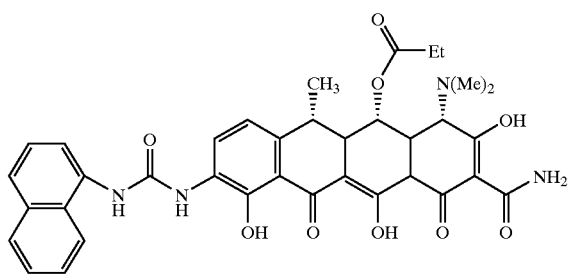
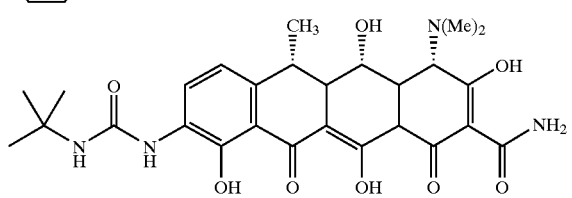
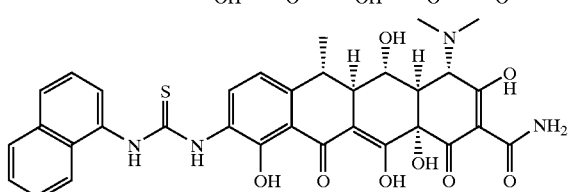
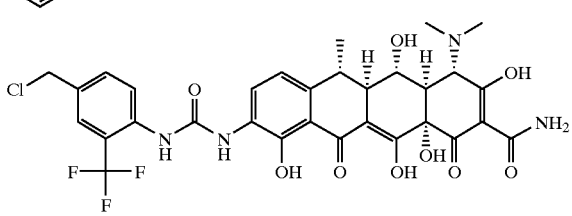
-continued
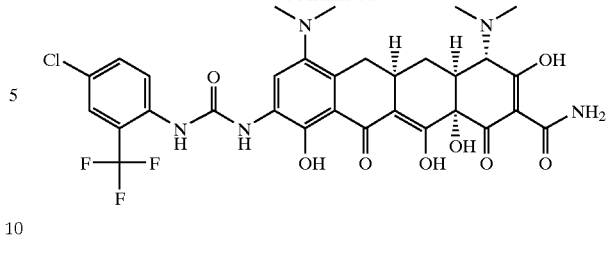
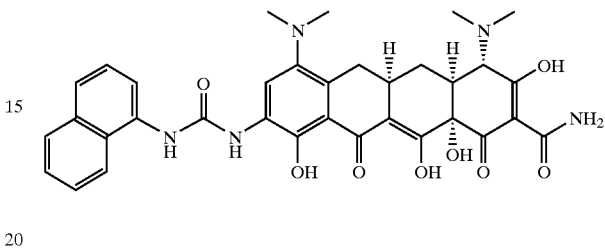
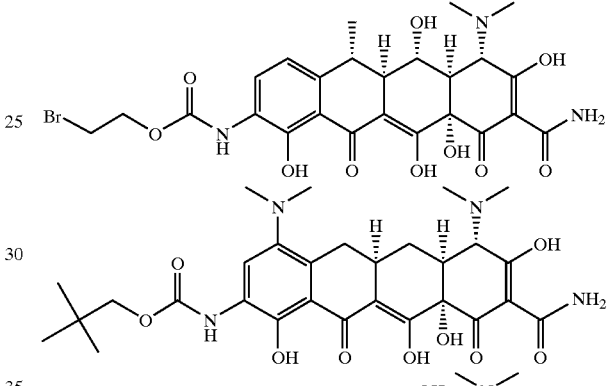
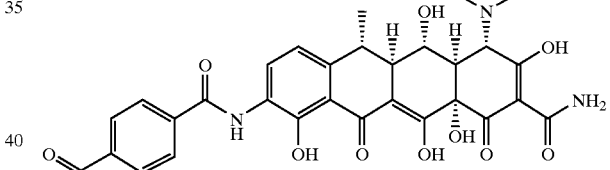
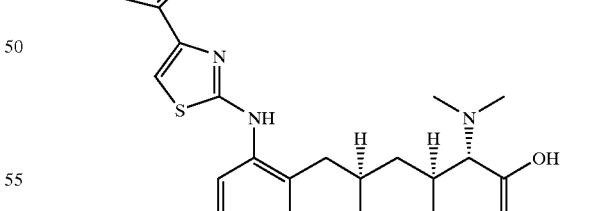
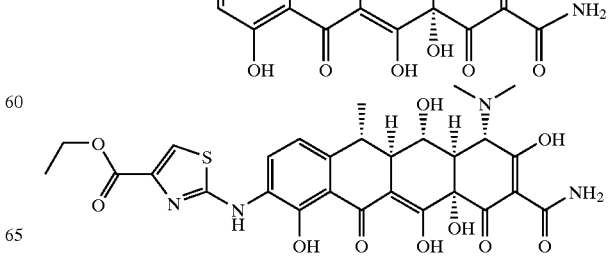

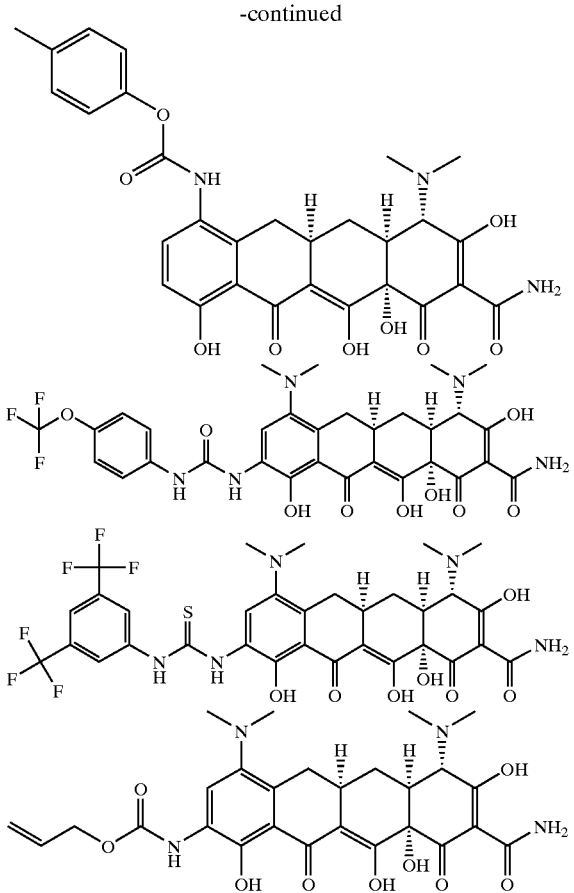

The invention includes methods for synthesizing 7- and/or 9-substituted tetracyacline compounds using reactive intermediates, such as thioureas, thiocarboxyamides, and diazonium salts, advantageously, at the $R^7$ and/or $R^9$ position of tetracycline compound of formula (I). In one embodiment, the invention pertains to methods of synthesizing 9- and/or 7-substituted tetracycline compounds by contacting a reactive intermediate with appropriate reagents under appropriate conditions, such that a 7- and/or 9-substituted tetracycline compound is formed. Examples of appropriate reagents and conditions are described in Schemes 1–3 and in Example 1.

The term "reactive intermediates" includes species which are generated during the synthesis of the 7- and/or 9-substituted tetracycline compounds of Formula (I). These intermediates may or may not be stable under reaction conditions and may or may not be isolatable. However, one of skill in the art can appreciate that these reactive intermediates can be used to generate other 7- and/or 9-substituted tetracycline compounds. The term "reactive intermediates" includes all intermediates which are synthesized or can be synthesized using the methodology discussed herein. Examples of reactive intermediates of the invention include 7- and/or 9-diazonium salts, 7- and/or 9-thiocarboxyamates, 7- and/or 9-anilino compounds, 7- and/or 9-amino tetracycline compounds, 7- and/or 9-nitro tetracycline compounds, 7- and/or 9-urea derivatives, 7- and/or 9-carbamate derivatives, etc.

The language "appropriate conditions" include conditions known in the art and conditions described herein to convert the reactive intermediate to a 7- and/or 9-substituted tetracycline compound of formula (I) or another desired tetracycline compound.

The language "appropriate reagents" include reagents known in the art and reagents described herein to convert the reactive intermediate to a tetracycline compound of formula (I) or another desired tetracycline compound.

In another embodiment, the invention includes methods of synthesizing 7- and/or 9-substituted tetracycline compounds outlined in the following schemes. Although in each scheme the reaction is shown for only one or two tetracycline compounds, one of skill in the art will appreciate that similar reactions can be also be performed with other tetracycline compounds.

In an embodiment, the invention pertains to a method for synthesizing 7- and/or 9-substituted tetracycline compounds by contacting an unsubstituted tetracycline compound with a nitrating agent, to form a 7- and/or 9-nitro substituted tetracycline compound. The 7- and/or 9-nitro substituted tetracycline compound is then hydrogenated with a hydrogenating agent to form a 7- and/or 9-amino substituted tetracycline compound. The 7- and/or 9-amino substituted tetracycline compound is contacted with an amino reactive compound, thereby forming a 7- and/or 9-substituted tetracycline compound.

The term "nitrating agent" includes compounds and chemicals which, under appropriate conditions, can introduce a nitro group (—$NO_2$) to a tetracycline compound. Advantageous nitrating agents include, for example, $NaNO_2$. Other methods of nitration are known in the art and are also included (see, for example, March, Advanced Organic Chemistry, John Wiley & Sons:New York, 1992, p. 522–525, and references cited therein). Advantageously, when the nitrating agent is $NaNO_2$, the reaction is conducted under acidic conditions.

The term "hydrogenating agent" includes compounds and chemicals which, under appropriate conditions, can convert a nitro group to an amino group (—$NH_2$). Examples of preferred hydrogenating agents include $H_2$ gas with a transition metal catalyst, advantageously, platinum. Other methods of converting nitro groups to amino groups are known in the art (see, for example March, Advanced Organic Chemistry, John Wiley & Sons:New York, 1992, p. 1216–1217, and references cited therein).

The term "amino reactive compound" includes compounds and molecules which can be reacted with the 7- and/or 9-amino tetracycline derivative to form a desired 7- and/or 9-substituted tetracycline compound, or a precursor thereof. Examples of advantageous amino reactive compounds for the formation of 9-substituted urea and carbamate tetracycline compounds include substituted and unsubstituted isocyanates and chloroformates. Scheme 1 below depicts the synthesis for a 9-substituted doxycycline compounds, but the methodology can be applied both to other tetracycline compounds and 7-substituted tetracycline compound. The depicted method includes treating an unsubstituted tetracycline compound (1—1) with acid (e.g., $H_2SO_4$) and a nitrating agent (e.g., sodium or potassium nitrate) to form the reactive nitro substituted tetracycline intermediate (1-2). The reactive nitro substituted tetracycline intermediate can be reduced to the corresponding amine (1-3) by hydrogenating reagents known in the art (e.g., hydrogen with metal catalysts, platinum oxide or the like) to produce the amino substituted tetracycline compound (1-3). The amino substituted tetracycline compound (1-3) can then be reacted in mild base with substituted isocyanates (1-4) to form mixed urea substituted tetracycline compounds (1-5). The amino substituted tetracycline compounds (1-3) can also be reacted with substituted or unsubstituted chloroformates (1-6) to form substituted carbamates tetracycline compounds (1-7). Additionally, the amino substituted tetracycline compounds (1-3) can be reacted with other species, such as the thioisocyanates (1-8), to form other desirable derivatives, such as the thioureas (1-9).

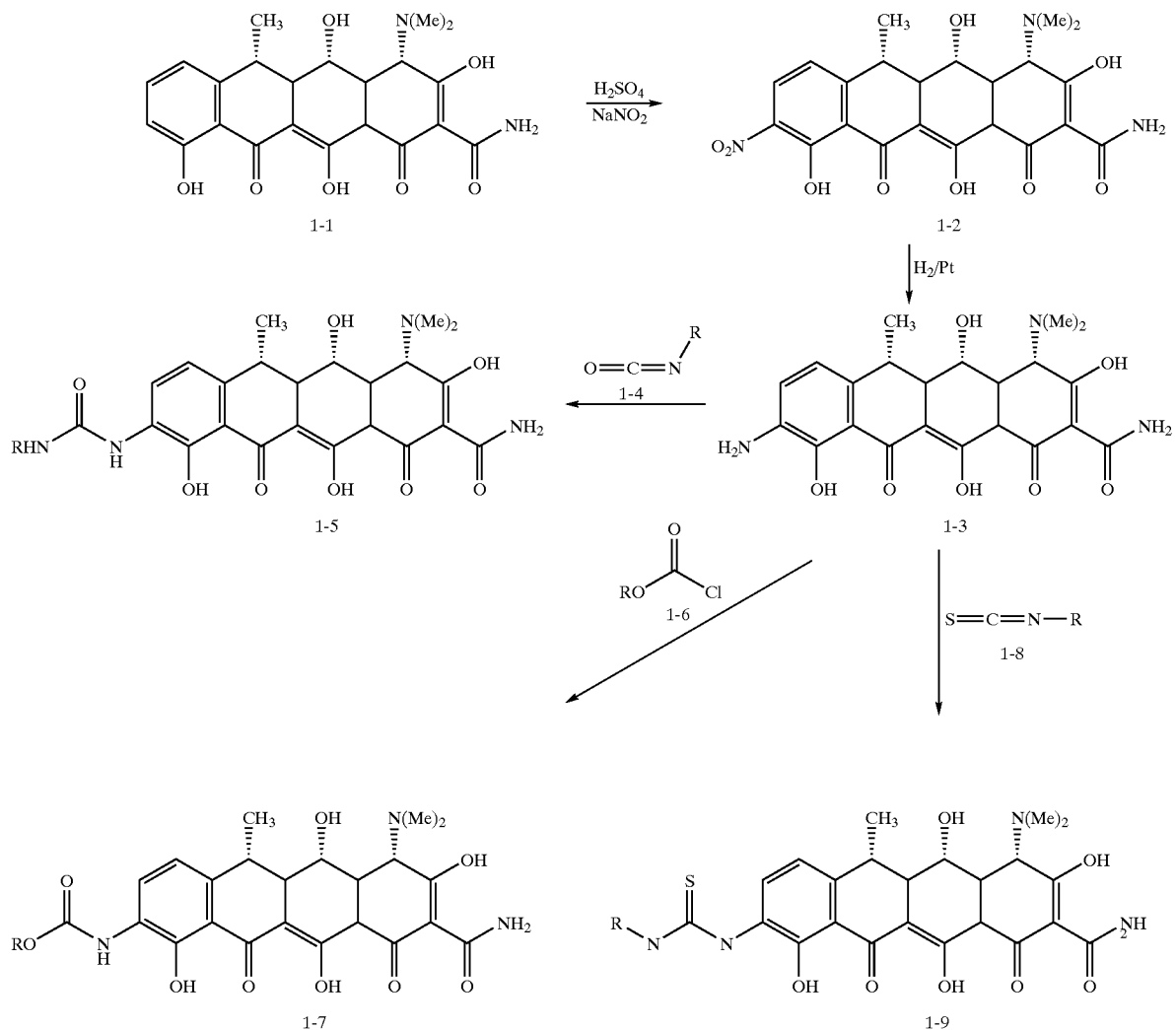

SCHEME 1

The initial nitration of the tetracycline compound may produce a mixture of the 7- and 9-substituted isomers. An ordinarily skilled artisan will be able to appreciate that the isomers can be separated by conventional methods after any of the reactions mentioned above. Techniques for separating isomers are well known in the art. For example, the amino substituted tetracycline compounds (e.g., 1-3) can be separated from other positional isomers by techniques known in the art, e.g., preparative HPLC on C18-reverse phase silica gel with a binary gradient system. The amino tetracycline compounds can also be prepared according to U.S. Pat. No. 3,483,251 through a reductive alkylation of 7-(N,N"-dicarbobenzyloxyhydrazino) tetracyclines. Furthermore, other 7- and/or 9-substituted tetracycline compounds can be synthesized by reacting the amino intermediate with amino reactive substrate.

The reactive 7- and/or 9-amino substituted tetracycline compounds are included as reactive intermediates. The amino substituted tetracycline compounds can react with other chemical species such as isocyanate derivatives or isothiocyanate derivatives to produce 7- and/or 9-position ureas and thioureas (thiocarbocarboxyamides) as shown in Scheme 1. The 7- and/or 9-position urea and thiourea tetracycline compounds are reactive intermediates and can be used in the synthesis of a wide variety of 7- and/or 9-substituted tetracycline compounds. For example, the 7- and/or 9-position thioureas can be used to form amino-heterocyclic moieties by reactions shown in Scheme 2, below.

SCHEME 2

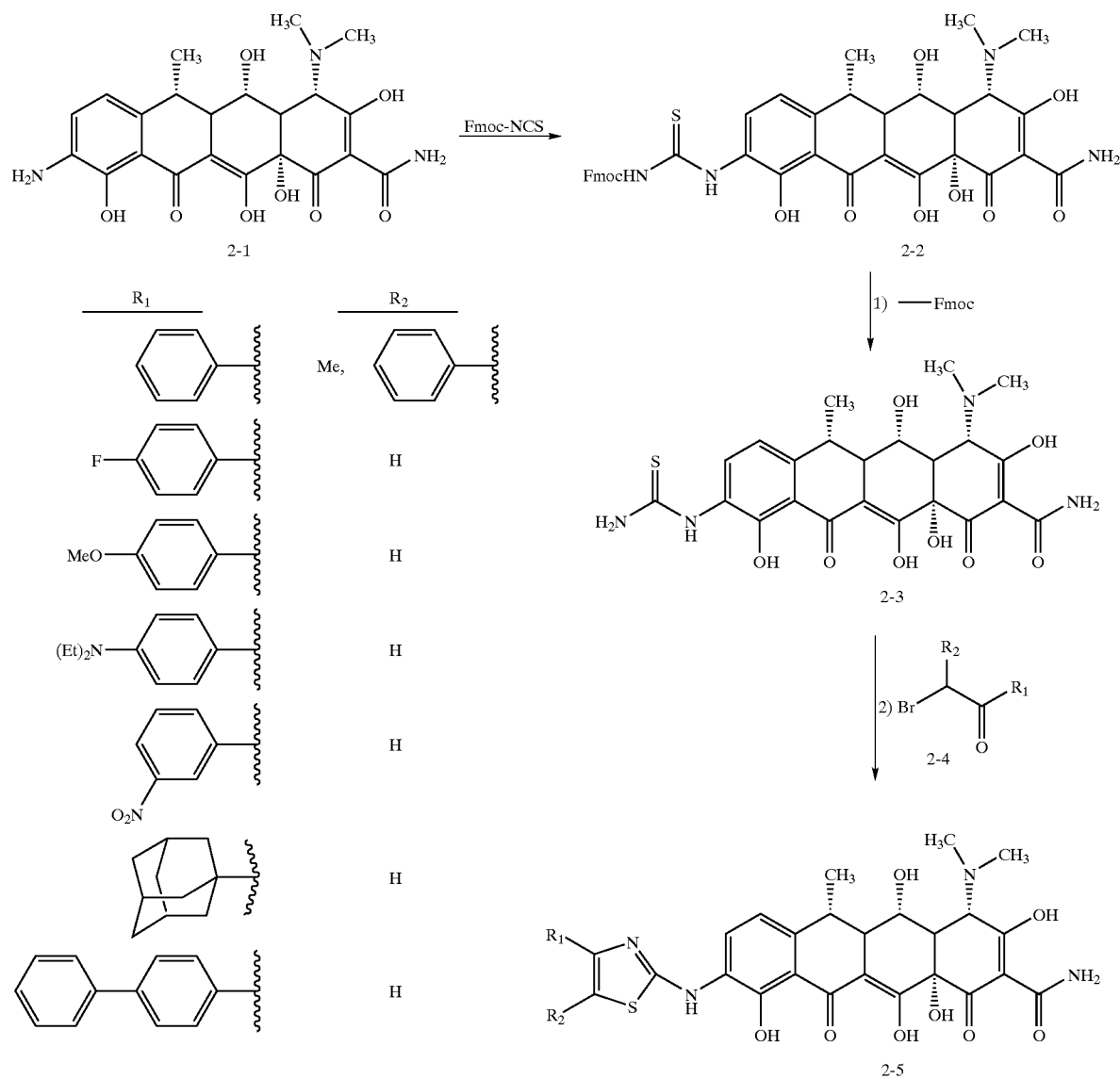

For example, 9-amino substituted tetracycline compound (2-1) can be reacted with Fmoc-NCS to produce a 9-Fmoc thiourea substituted tetracycline compound (2-2). The Fmoc substituted thiourea substituted tetracycline compound (2-2) can be deprotected using methods known in the art to form the 9-thiourea substituted tetracycline compound (2-3). The 9-thiourea substituted tetracycline compound (2-3) is a reactive intermediate, which can be reacted with α-haloketones (2-4, e.g., substituted or unsubstituted α-haloketones, etc.), to produce 9-thiazolylamino substituted tetracycline compounds (2-5). This methodology can also be used to form 7-position thiourea substituted tetracycline reactive intermediates as well as 7-position thiazolylamino tetracycline compounds.

Thiourea tetracycline reactive intermediates also can be used as reactive intermediates in the synthesis of, for example, spiro and fused cyclopentapyrozole and pyrimidine derivatives (Albar et al., *J. Chem. Res., Synop.*, (2), 40–41 (1997); pyridazinedione derivatives (Sharaf El-Din, *Alexandria J. Pharm. Sci.*, 11(1) 9–12 (1997)); benzothiazole acrylic acid derivatives (Kassem, et al., Pak. *J. Sci. Ind. Res.* 38 (11–12) 424–427 (1995)); thiazoline, aryazothioazole and pyrazole derivatives (Abdelhamid, A. *Phosphorous, Sulfur, Silicon Related Elem.* 119 (181–191) (1996)); pyrimidine derivatives (Fikry, *J. Indian Chem. Soc.*, 73(12), 698–699 (1996)); aminothiazole-carbonitrile derivatives (Shiono, JP 95-331456); benzimidazole derivatives (Omar et al. *Egypt. J. Pharm. Sci.* 37(1–6), 609–620 (1996)); benzylthiazolidine derivatives (Morita et al., JP 95-200268); clonidine derivatives (Pierce, et al. WO 95/21818); pyrimidine derivatives (Nassar, et al. *Egypt. J. Chem.*, 40(3) 239–247 (1997)); bicyclic derivatives (Zhu, et al. *Hanneng Cailiao* 5(4), 165–170 (1997)); combinatorial libraries (Nefzi, et al. WO 98/19693); triazinoindole derivatives (Tomchin, et al. *Khim. -Farm. Zh.*, 31(3), 19–27 (1997); Tomchin et al., *Khim. -Farm. Zh.*, 32(3) 7–10 (1998)); aryl thio derivatives (Chikalia, et al. *Proc. Nat. Acad. Sci. India* 68(A), I, 1998); and α-amino acid derivatives (Beyer, et al. *Tetrahedron*, 52(17) 6233–6240 (1996)).

SCHEME 3

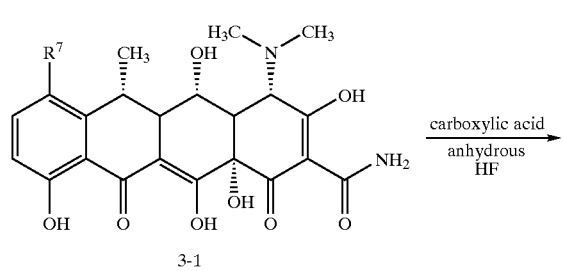

3-1

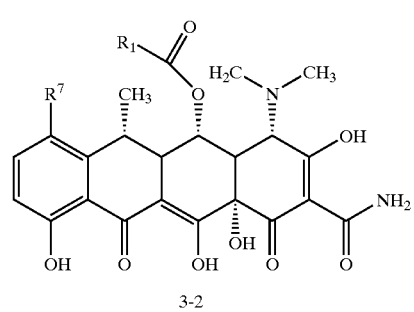

3-2

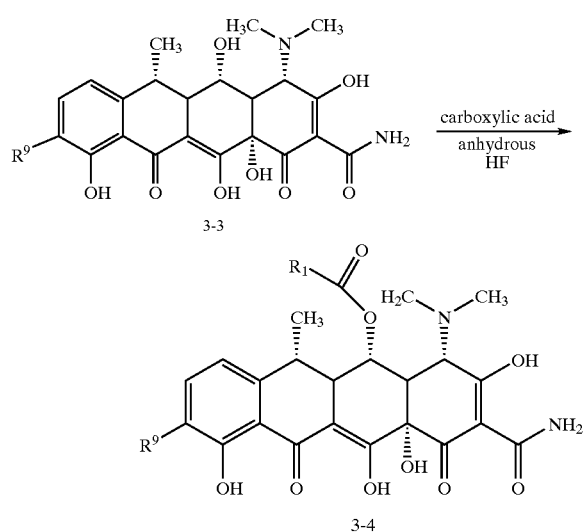

3-3

3-4

As depicted in Scheme 3, 5-esters of 7- and/or 9-substituted tetracycline compounds (3-1 and 3-3) can be formed by dissolving the 7- and/or 9-substituted tetracycline compounds in strong acid and adding the appropriate carboxylic acid. Examples of strong acids include anhydrous hydrogen fluoride, methanesulphonic acid, and trifluoromethanesulfonic acid.

The invention also pertains to a method for synthesizing a 7- or 9-substituted tetracycline compound of formula (I), by contacting a reactive intermediate with appropriate reagents under appropriate conditions, such that a substituted tetracycline compound is formed. The compound of formula (I) is:

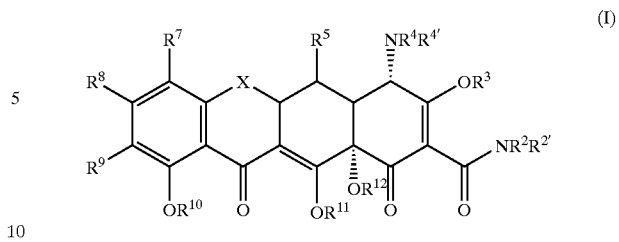

(I)

wherein:

X is $CHC(R^{13}Y'Y)$, $CR^{6'}R^6$, S, $NR^6$, or O;

$R^2$ is hydrogen, alkyl, alkynyl, alkoxy, alkylthio, alkylsulfinyl, alkylsulfonyl, alkylamino, arylalkyl, aryl, heterocyclic, heteroaromatic or a prodrug moiety;

$R^4$ and $R^{4'}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{2'}$, $R^3$, $R^{10}$, $R^{11}$ and $R^{12}$ are each hydrogen or a pro-drug moiety;

$R^5$ is hydrogen, hydroxyl, or a prodrug moiety;

$R^6$, $R^{6'}$, and $R^8$ are each independently hydrogen, alkyl, alkenyl, alkynyl, aryl, alkoxy, alkylthio, alkylsulfinyl, alkylsulfonyl, alkylamino, arylalkyl, or halogen;

$R^7$ is hydrogen, dialkylamino, heteroaryl-amino, or $NR^{7c}C(=W')WR^{7a}$;

$R^{13}$ is hydrogen, hydroxy, alkyl; alkenyl; alkynyl; alkoxy; alkylthio; alkylsulfinyl; alkylsulfonyl; alkylamino; or an arylalkyl;

Y' and Y are each independently hydrogen; halogen; hydroxyl; cyano, sulfhydryl; amino; alkyl; alkenyl; alkynyl; alkoxy; alkylthio; alkylsulfinyl; alkylsulfonyl; alkylamino; or an arylalkyl;

$R^9$ is hydrogen, $NR^{9c}C(=Z')ZR^{9a}$, or heteroaryl-amino;

Z is $CR^{9d}R^{9e}$, $NR^{9b}$, or O;

Z' is O or S;

$R^{9a}$, $R^{9b}$, $R^{9c}$, $R^{9d}$, and $R^{9e}$ are each independently hydrogen, alkyl, alkenyl, alkynyl, alkoxy, alkylthio, alkylsulfinyl, alkylsulfonyl, arylsulfonyl, alkoxycarbonyl, arylcarbonyl, alkylamino, arylalkyl, aryl, heterocyclic, heteroaromatic, absent, or a prodrug moiety;

W is $CR^{7d}R^{7e}$, $NR^{7b}$ or O;

W' is O or S; and $R^{7a}$, $R^{7b}$, $R^{7c}$, $R^{7d}$, and $R^{7e}$ are each independently hydrogen, alkyl, alkenyl, alkynyl, alkoxy, alkylthio, alkylsulfinyl, arylsulfonyl, alkoxycarbonyl, arylcarbonyl, alkylamino, arylalkyl, aryl, heterocyclic, heteroaromatic, absent, or a prodrug moiety;

and pharmaceutically acceptable salts thereof, provided that $R^9$ is not hydrogen when $R^7$ is dialkylamino or hydrogen.

In one embodiment, the reactive intermediate is a 7- and/or 9-diazonium salt, a 7- and/or 9-nitro compound, a 7- and/or 9-thiourea, or a 7- and/or 9-thiocarboxamide.

The invention also pertains to reactive intermediates of the formula:

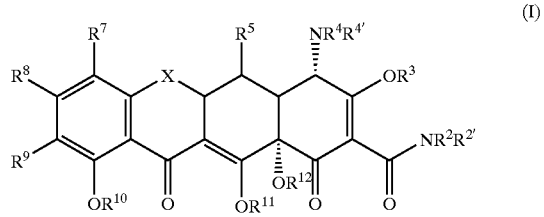

(I)

wherein:

X is CHC($R^{13}$Y'Y), CHR$^6$, S, NR$^6$, or O;

R$^2$ is hydrogen, alkyl, alkynyl, alkoxy, alkylthio, alkylsulfinyl, alkylsulfonyl, alkylamino, arylalkyl, aryl, heterocyclic, heteroaromatic or a prodrug moiety;

R$^4$ and R$^{4'}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R$^{2'}$, R$^3$, R$^{10}$, R$^{11}$ and R$^{12}$ are each hydrogen or a pro-drug moiety;

R$^5$ is hydrogen, hydroxyl, or a prodrug moiety;

R$^6$ and R$^8$ are each independently hydrogen, alkyl, alkenyl, alkynyl, aryl, alkoxy, alkylthio, alkylsulfinyl, alkylsulfonyl, alkylamino, or an arylalkyl;

R$^{13}$ is hydrogen, hydroxy, alkyl; alkenyl; alkynyl; alkoxy; alkylthio; alkylsulfinyl; alkylsulfonyl; alkylarnino; or an arylalkyl;

Y' and Y are each independently hydrogen; halogen; hydroxyl; cyano, sulfhydryl; amino; alkyl; alkenyl; alkynyl; alkoxy; alkylthio; alkylsulfinyl; alkylsulfonyl; alkylamino; or an arylalkyl;

R$^9$ is hydrogen, thiourea, diazonium salt, thiocarboxamide, or nitro;

R$^7$ is hydrogen, thiourea, dialkylamino, diazonium salt, thiocarboxamide, or nitro; and pharmaceutically acceptable salts thereof, provided that R$^9$ is not hydrogen when R$^7$ hydrogen or dialkylamino.

In a further embodiment, R$^7$ is hydrogen or dialkylamino, when R$^9$ is thiourea, diazonium salt, thiocarboxamide, or a nitro moiety. In another, R$^9$ is hydrogen when R$^7$ is thiourea, diazonium salt, thiocarboxamide, or a nitro moiety.

Unless specifically indicated, the chemical groups of the present invention may be substituted or unsubstituted. Further, unless specifically indicated, the chemical substituents may in turn be substituted or unsubstituted. In addition, multiple substituents may be present on a chemical group or substituent. Examples of substituents include alkyl, alkenyl, alkynyl, halogen, hydroxyl, alkylcarbonyloxy, arylcarbonyloxy, alkoxycarbonyloxy, aryloxycarbonyloxy, carboxyl, alkylcarbonyl, arylcarbonyl, alkoxycarbonyl, aminocarbonyl, alkylaminocarbonyl, dialkylaminocarbonyl, alkylthiocarbonyl, alkoxyl, formyl, trimethylsilyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amido, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, aromatic or heteroaromatic moieties, cholesterol, arylsulfonyl, azo, thiazolyl, adamantyl, and phosphonyl.

The term "alkyl" includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In an embodiment, a straight chain or branched chain alkyl has 10 or fewer carbon atoms in its backbone (e.g., $C_1$–$C_{10}$ for straight chain, $C_3$–$C_{10}$ for branched chain), and in another embodiment, 4 or fewer. Likewise, in certain embodiments, cycloalkyls have from 4–7 carbon atoms in their ring structure, and may have 5 or 6 carbons in the ring structure.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" moiety is an alkyl substituted with an aryl (e.g., phenylmethyl (benzyl)).

The term "aryl" includes aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The terms "alkenyl" and "alkynyl" include unsaturated aliphatic groups analogous in length and possible substitution to the alkyls described above, but that contain at least one double or triple bond, respectively.

Unless the number of carbons is otherwise specified, "lower alkyl" as used herein means an alkyl group, as defined above, but having from one to five carbon atoms in its backbone structure. Likewise, "lower alkenyl" and "lower alkynyl" have similar chain lengths.

The terms "alkoxyalkyl", "polyaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The terms "polycyclyl," "multicycle" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety. Examples of "multicyclic" moieties include steroids, such as, for example, cholesterol.

The term "heteroatom" as used herein means an atom of any element other than carbon or hydrogen. Preferred heteroatoms are nitrogen, oxygen, sulfur and phosphorus.

Suitable alkanoyl groups include groups having 1 to about 4 or 5 carbonyl groups. Suitable aroyl groups include groups having one or more carbonyl groups as a substituent to an aryl group such as phenyl or other carbocyclic aryl. Suitable alkaroyl groups have one or more alkylcarbonyl groups as a substituent to an aryl group such as phenylacetyl and the like. Suitable carbocyclic aryl groups have 6 or more carbons such as phenyl, naphthyl and the like. Suitable aryloyl groups are carbocyclic aryl groups that are substituted with one or more carbonyl groups, typically 1 or 2 carbonyl groups.

Prodrugs are compounds which are converted in vivo to active forms (see, e.g., R. B. Silverman, 1992, "The Organic Chemistry of Drug Design and Drug Action", Academic Press, Chp. 8). Prodrugs can be used to alter the biodistribution (e.g., to allow compounds which would not typically enter the reactive site of the protease) or the pharmacokinetics for a particular compound. For example, a hydroxyl group, can be esterified, e.g., with a carboxylic acid group to yield an ester. When the ester is administered to a subject, the ester is cleaved, enzymatically or non-enzymatically, reductively or hydrolytically, to reveal the hydroxyl group.

The language "prodrug moiety" includes moieties which can be metabolized in vivo to yield an active compound. For example, the term includes moieties which can modify certain functional groups of the substituted tetracycline compounds, such as, but not limited to, hydroxyl groups and amino groups. In an embodiment, the prodrugs moieties are metabolized in vivo by esterases or by other mechanisms to hydroxyl groups, amino, amido or other groups which allow the substituted tetracycline compound to perform its intended function. Examples of prodrugs and their uses are well known in the art (See, e.g., Berge et al. (1977) "Pharmaceutical Salts", *J. Pharm. Sci.* 66:1–19). Some prodrugs can be prepared in situ during the final isolation and purification of the compounds, or by separately reacting the purified compound in its free acid form or hydroxyl with a suitable esterifying agent. Hydroxyl groups, for example, can be converted into esters via treatment with a carboxylic acid (see, for example, Scheme 3). Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g, with methyl, halo, or methoxy substituents) aryl and aryl-lower alkyl esters, amides, lower-alkyl amides, di-lower alkyl amides, and hydroxy amides. Preferred prodrug moieties for hydroxyl groups are propionoic acid esters and acyl esters. Amino or amido groups can be modified by methods known in the art to form Schiff bases and other prodrugs which may or may not be metabolized in vivo.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis.

The invention also features a method for treating a tetracycline compound responsive state in a subject, by administering to the subject a substituted tetracycline compound of the invention. Preferably, an effective amount of the substituted tetracycline compound is administered. In an embodiment, the substituted tetracycline compound is of formula (I). The invention includes methods of treating a tetracycline compound responsive state using any one of the compounds described above or found in Table 2, below.

The term "subject" includes any animal or plant which is capable of being treated or may obtain some benefit from the administration of a substituted tetracycline compound of the invention. The term also include animals (e.g., birds, reptiles, fish, mammals, (e.g., cows, pigs, sheep, horses, cows, dogs, cats, squirrels, bears, monkeys, chimpanzees, gorillas, goats, ferrets, and, preferably, humans). The subject may be currently suffering from the tetracycline compound responsive state or may be at risk of suffering from the tetracycline compound responsive state. In an embodiment, the subject may be immunocomprimised, e.g., suffering from AIDS, undergoing or recovering from chemotherapy, or have an immune disorder.

The language "tetracycline compound responsive state" includes state which can be treated, prevented, or otherwise ameliorated by the administration of a substituted tetracycline compound of the invention. Tetracycline compound responsive states include bacterial infections (including those which are resistant to other tetracycline compounds), cancer, diabetes, and other states for which tetracycline compounds have been found to be active (see, for example, U.S. Pat. Nos. 5,789,395; 5,834,450; and 5,532,227). Compounds of the invention can be used to prevent or control important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., *Cancer Res.,* 48:6686–6690 (1988)).

Bacterial infections may be caused by a wide variety of gram positive and gram negative bacteria. The compounds of the invention are usefuil as antibiotics against organisms which are resistant to other tetracycline compounds. The antibiotic activity of the tetracycline compounds of the invention may be determined using the method discussed in Example 2, or by using the in vitro standard broth dilution method described in Waitz, J. A., *National Commissionfor Clinical Laboratory Standards, Document* M7-A2, vol. 10, no. 8, pp. 13–20, $2^{nd}$ edition, Villanova, Pa. (1990).

The tetracycline compounds may also be used to treat infections traditionally treated with tetracycline compounds such as, for example, rickettsiae; a number of gram-positive and gram-negative bacteria; and the agents responsible for lymphogranuloma venereum, inclusion conjunctivitis, psittacosis. The substituted tetracycline compounds may be used to treat infections of pneumococci, Salmonella, *E. coli, S. aureus, E. hirae* or *E. faecalis*. In one embodiment, the substituted tetracycline compound is used to treat a bacterial infection that is resistant to other unsubstituted tetracycline antibiotic compounds (e.g., tetracycline compounds such as doxycycline, minocycline, sancycline, or tetracycline). In another embodiment, the substituted tetracycline compounds of the invention are less cytotoxic to the subject as compared to unsubstituted tetracycline compounds, such that the substituted tetracycline compounds may be given at a higher dosage with out being fatal or excessively toxic to the subject. The substituted tetracycline compound of the invention may be administered with a pharmaceutically acceptable carrier.

Examples of compounds of the invention which may advantageously be used in the methods of the invention include substituted tetracycline compounds of formula (I), as well as compounds described in Table 2. Examples of compounds of the invention include: Doxycycline 9-carbamic acid 9H-fluoren-9-ylmethyl ester; (9-(Naphthyn-1-yl) doxycycline urea; 9-(3-Methyl-1-butyl) doxycycline urea; 9-Phenyl doxycycline urea; 9-t-Butyl doxycycline urea; FMOC 9-amino doxycycline; 9-(4'-Chloro-2'-trifluoromethylphenyl) doxycycline urea; 9-(4'-Fluorophenyl) doxycycline carbamate; 9-(4'-Methoxyphenyl) doxycycline carbamate; 9-BOC amino doxycycline; 9-(Phenylthiazolyl) amino doxycycline; 9-(Ethylthiazolyl) amino doxycycline; (4-Fluorophenylthiazolyl) amino doxycycline; 9-(4'-Methoxyphenylthiazolyl) amino doxycycline; 9-(3'-Nitrophenylthiazolyl) amino doxycycline; 9-(4'-Methyl, 5'-phenylthiazolyl) amino doxycycline; 9-Neopentyl minocycline carbamate; 9-(Phenylthiazolyl) amino sancycline; 9-(Adamantylthiazolyl) amino doxycycline; 9-(Naphthyn-1-yl urea) Doxycycline 5-propanoic acid ester; Doxycycline 9-Thiocarbamic acid 9H-fluoren-9-ylmethyl ester; (9-(Naphthyn-1-yl) doxycycline thiourea; 9-(3-methyl-1-butyl) doxycycline thiourea; 9-Phenyl doxycycline thiourea; 9-t-Butyl doxycycline thiourea; 9-(4'-Chloro-2'-trifluoromethylphenyl) doxycycline thiourea; 9-(4'-Fluorophenyl) doxycycline thiocarbamate; 9-(4-Methoxyphenyl) doxycycline thiocarbamate; 9-Neopentyl minocycline thiocarbamate; 9-(Naphthyn-1-yl) doxycycline thiourea 5-propanoic acid ester; Minocycline 9-carbamic acid 9H-fluoren-9-ylmethyl ester; (9-(Naphthyn-1-yl) minocycline urea; 9-(3-Methyl-1-butyl) minocycline urea; 9-Phenyl doxycycline urea; 9-t-Butyl minocycline urea; FMOC 9-amino minocycline; 9-(4'-Chloro-2'-trifluoromethylphenyl) minocycline urea; 9-(4'-Fluorophenyl) minocycline carbamate; 9-(4'-Methoxyphenyl) minocycline carbamate; 9-BOC amino minocycline; 9-(Phenylthiazolyl) amino minocycline; 9-(Ethylthiazolyl) amino minocycline; (4'-Fluorophenylthiazolyl) amino minocycline; 9-(4'-Methoxyphenylthiazolyl) amino minocycline; 9-9-(3'-Nitrophenylthiazolyl) amino minocycline; 9-(4'-Methyl, 5'-phenylthiazolyl) amino doxycycline; 9-Neopentyl doxycycline carbamate; 9-(Phenylthiazolyl) amino minocycline; 9-(Adamantylthiazolyl) amino minocycline; Minocycline 9-thiocarbamic acid 9H-fluoren-9-ylmethyl ester; (9-(Naphthyn-1-yl) minocycline thiourea; 9-(3'-Methyl-1-butyl) minocycline thiourea; 9-Phenyl minocycline thiourea; 9-t-Butyl minocycline thiourea; 9-(4'-Fluorophenyl) minocycline thiocarbamate; 9-(4'-Methoxyphenyl) minocycline thiocarbamate; 9-Neopentyl doxycycline thiocarbamate; 9-(2'-Bromoethyl) doxycycline carbamate; 9-(n-Pentyl) minocycline carbamate; 9-(4'-Benzoylbenzoyl) amino doxycycline; 7-(3'-Nitrophenylthiazolyl) amino sancycline; 9-(3'-Ethoxycarbonylthiazolyl) amino doxycycline; 7-(4'-Methylphenyl) sancycline carbamate; 9-(4'-Trifluoromethoxyphenyl) minocycline urea; 9-(3',5'-diperfluorophenyl) minocycline thiourea; 9-Prop-2'-enyl minocycline carbamate; 9-(4'-Chloro, 2'-nitrophenyl) minocycline urea; 9-Ethyl minocycline carbamate; 9-n-Butyl minocycline carbamate; 9-n-But-3-enyl minocycline carbamate; Doxycycline 7-carbamic acid 7H-fluoren-7-ylmethyl ester; 7-(Naphthyn-1-yl) doxycycline urea; 7-(3-Methyl-1-butyl) doxycycline urea; 7-Phenyl doxycycline urea; 7-t-Butyl doxycycline urea; 7-Fmoc amino doxycycline; 7-(4'-Chloro-2-trifluoromethylphenyl) doxycycline urea; 7-(4'-Fluorophenyl) doxycycline carbamate; 7-(4'-Methoxyphenyl) doxycycline carbamate; 7-BOC amino doxycycline; 7-(3'Phenylthiazolyl) amino doxycycline; 7-(3'-Ethylthiazolyl) amino doxycycline; 7-(4"-Fluorophenylthiazolyl) amino doxycycline; 7-(4"-Methoxyphenylthiazolyl) amino doxycycline; 7-(Phenylthiazolylamino)-sancycline; 7-(3'-Nitrophenylthiazolyl) amino doxycycline; 7-(4'-Methyl, 5'-phenylthiazolyl) amino doxycycline; 7-(Adamantylthiazolyl) amino doxycycline; Doxycycline 7-thiocarbamic acid 7H-fluoren-7-ylmethyl ester; 7-(Naphthyn-1-yl) doxycycline thiourea; 7-(3-Methyl-1-butyl) doxycycline thiourea; 7-Phenyl amino doxycycline thiourea; 7-t-butyl amino doxycycline thiourea; 7-(4'-Chloro-2'-trifluoromethylphenyl) doxycycline thiourea; 7-(4'-Fluorophenyl) doxycycline thiocarbamate; 7-(4'-Methoxyphenyl) doxycycline thiocarbamate; 7-(Naphthyn-1-yl) doxycycline urea 5-propanoic acid ester; 7-(Naphthyn-1-yl) doxycycline thiourea 5-propanoic acid ester; 9-i-Butyl minocycline carbamate, and pharmaceutically acceptable salts and prodrugs thereof.

The language "effective amount" of the substituted tetracycline compound is that amount necessary or sufficient to treat or prevent a tetracycline compound responsive state. The effective amount can vary depending on such factors as the size and weight of the subject, the type of illness, or the particular substituted tetracycline compound. For example, the choice of the substituted tetracycline compound can affect what constitutes an "effective amount". One of ordinary skill in the art would be able to study the aforementioned factors and make the determination regarding the effective amount of the substituted tetracycline compound without undue experimentation.

The invention also pertains to methods of treatment against microorganism infections and associated diseases. The methods include administration of an effective amount of one or more substituted tetracycline compounds to a subject. The subject can be either a plant or, advantageously, an animal, e.g., a mammal, e.g., a human.

In the therapeutic methods of the invention, one or more substituted tetracycline compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof.

In one embodiment, the invention pertains to pharmaceutical compositions which comprise one or more substituted tetracycline compounds of the invention, as described above. The invention pertains to pharmaceutical compositions which comprise any of the substituted tetracycline compounds described in this application. For example, the invention pertains to pharmaceutical compositions which comprise substituted tetracycline compounds of both Formula (I) and Table 2. Other examples of substituted tetracycline compounds of the invention which may be included in the pharmaceutical compositions of the invention include, but are not limited to:

Doxycycline 9-carbamic acid 9H-fluoren-9-ylmethyl ester; (9-(Naphthyn-1-yl) doxycycline urea; 9-(3-Methyl-1-butyl) doxycycline urea; 9-Phenyl doxycycline urea; 9-t-Butyl doxycycline urea; FMOC 9-amino doxycycline; 9-(4'-Chloro-2'-trifluoromethylphenyl) doxycycline urea; 9-(4'-Fluorophenyl) doxycycline carbamate; 9-(4'-Methoxyphenyl) doxycycline carbamate; 9-BOC amino doxycycline; 9-(Phenylthiazolyl) amino doxycycline; 9-(Ethylthiazolyl) amino doxycycline; (4-Fluorophenylthiazolyl) amino doxycycline; 9-(4'-Methoxyphenylthiazolyl) amino doxycycline; 9-(3'-Nitrophenylthiazolyl) amino doxycycline; 9-(4'-Methyl, 5'-phenylthiazolyl) amino doxycycline; 9-Neopentyl minocycline carbamate; 9-(Phenylthiazolyl) amino sancycline; 9-(Adamantylthiazolyl) amino doxycycline; 9-(Naphthyn-1-yl urea) Doxycycline 5-propanoic acid ester; Doxycycline 9-Thiocarbamic acid 9H-fluoren-9-ylmethyl ester; (9-(Naphthyn-1-yl) doxycycline thiourea; 9-(3-methyl-1-butyl) doxycycline thiourea; 9-Phenyl doxycycline thiourea; 9-t-Butyl doxycycline thiourea; 9-(4'-Chloro-2'-trifluoromethylphenyl) doxycycline thiourea; 9-(4'-Fluorophenyl) doxycycline thiocarbamate; 9-(4-Methoxyphenyl) doxycycline thiocarbamate; 9-Neopentyl minocycline thiocarbamate; 9-(Naphthyn-1-yl) doxycycline thiourea 5-propanoic acid ester; Minocycline 9-carbamic acid 9H-fluoren-9-ylmethyl ester; (9-(Naphthyn-1-yl) minocycline urea; 9-(3-Methyl-1-butyl) minocycline urea; 9-Phenyl doxycycline urea; 9-t-Butyl minocycline urea; FMOC 9-amino minocycline; 9-(4'-Chloro-2'-trifluoromethylphenyl) minocycline urea; 9-(4'-Fluorophenyl) minocycline carbamate; 9-(4'-Methoxyphenyl) minocycline carbamate; 9-BOC amino minocycline; 9-(Phenylthiazolyl) amino minocycline; 9-(Ethylthiazolyl) amino minocycline; (4'-Fluorophenylthiazolyl) amino minocycline; 9-(4'-Methoxyphenylthiazolyl) amino minocycline; 9-9-(3'-Nitrophenylthiazolyl) amino minocycline; 9-(4'-Methyl, 5'-phenylthiazolyl) amino doxycycline; 9-Neopentyl doxycycline carbamate; 9-(Phenylthiazolyl) amino minocycline; 9-(Adamantylthiazolyl) amino minocycline; Minocycline 9-thiocarbamic acid 9H-fluoren-9-ylmethyl ester; (9-(Naphthyn-1-yl) minocycline thiourea; 9-(3'-Methyl-1-butyl) minocycline thiourea; 9-Phenyl minocycline thiourea; 9-t-Butyl minocycline thiourea; 9-(4'-Fluorophenyl) minocycline thiocarbamate; 9-(4'-Methoxyphenyl) minocycline thiocarbamate; 9-Neopentyl doxycycline thiocarbamate; 9-(2'-Bromoethyl) doxycycline carbamate; 9-(n-Pentyl) minocycline carbamate; 9-(4'-Benzoylbenzoyl) amino doxycycline; 7-(3'-Nitrophenylthiazolyl) amino sancycline; 9-(3'-Ethoxycarbonylthiazolyl) amino doxycycline; 7-(4'-Methylphenyl) sancycline carbamate; 9-(4'-Trifluoromethoxyphenyl) minocycline urea; 9-(3',5'-diperfluorophenyl) minocycline thiourea; 9-Prop-2'-enyl minocycline carbamate; 9-(4'-Chloro, 2'-nitrophenyl) minocycline urea; 9-Ethyl minocycline carbamate; 9-n-Butyl minocycline carbamate; 9-n-But-3-enyl minocycline carbamate; Doxycycline 7-carbamic acid 7H-fluoren-7-ylmethyl ester; 7-(Naphthyn-1-yl) doxycycline urea; 7-(3-Methyl-1-butyl) doxycycline urea; 7-Phenyl doxycycline urea; 7-t-Butyl doxycycline urea; 7-Fmoc amino doxycycline; 7-(4'-Chloro-2-trifluoromethylphenyl) doxycycline urea; 7-(4'-Fluorophenyl) doxycycline carbamate; 7-(4'-Methoxyphenyl) doxycycline carbamate; 7-BOC amino doxycycline; 7-(3'Phenylthiazolyl) amino doxycycline; 7-(3'-Ethylthiazolyl) amino doxycycline; 7-(4"-Fluorophenylthiazolyl) amino doxycycline; 7-(4"-Methoxyphenylthiazolyl) amino doxycycline; 7-(Phenylthiazolylamino)-sancycline; 7-(3'-Nitrophenylthiazolyl) amino doxycycline; 7-(4'-Methyl, 5'-phenylthiazolyl) amino doxycycline; 7-(Adamantylthiazolyl) amino doxycycline; Doxycycline 7-thiocarbamic acid 7H-fluoren-7-ylmethyl ester; 7-(Naphthyn-1-yl) doxycycline thiourea; 7-(3-Methyl-1-butyl) doxycycline thiourea; 7-Phenyl amino doxycycline thiourea; 7-t-butyl amino doxycycline thiourea; 7-(4'-Chloro-2'-trifluoromethylphenyl) doxycycline thiourea; 7-(4'-Fluorophenyl) doxycycline thiocarbamate; 7-(4'-Methoxyphenyl) doxycycline thiocarbamate; 7-(Naphthyn-1-yl) doxycycline urea 5-propanoic acid ester; 7-(Naphthyn-1-yl) doxycycline thiourea 5-propanoic acid ester; 9-i-Butyl minocycline carbamate, and pharmaceutically acceptable salts and prodrugs thereof.

The language "pharmaceutically acceptable carrier" includes substances capable of being coadministered with the substituted tetracycline compound(s), and which allow the substituted tetracycline compound to perform its intended function, e.g., treat or prevent a tetracycline compound responsive state. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The substituted tetracycline compounds of the invention that are basic in nature are capable of forming a wide variety of salts with various inorganic and organic acids. The acids that may be used to prepare pharmaceutically acceptable acid addition salts of the tetracycline compounds of the invention that are basic in nature are those that form nontoxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a tetracycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The substituted tetracycline compounds of the invention that are acidic in nature are capable of forming a wide variety of base salts. The chemical bases that may be used as reagents to prepare pharmaceutically acceptable base salts of those substituted tetracycline compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of tetracycline compounds of the invention that are acidic in nature may be formed with pharmaceutically acceptable cations by conventional methods. Thus, these salts may be readily prepared by treating the tetracycline compound of the invention with an aqueous solution of the desired pharmaceutically acceptable cation and evaporating the resulting solution to dryness, preferably under reduced pressure. Alternatively, a lower alkyl alcohol solution of the substituted tetracycline compound of the invention may be mixed with an alkoxide of the desired metal and the solution subsequently evaporated to dryness.

The preparation of other tetracycline compounds of the invention not specifically described in the foregoing experimental section can be accomplished using combinations of the reactions described above that will be apparent to those skilled in the art.

The substituted tetracycline compounds of the invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The pharmaceutical compositions of the invention may be administered alone or in combination with other known compositions for treating tetracycline responsive states in a mammal. Preferred mammals include pets (e.g., cats, dogs, ferrets, etc.), farm animals (cows, sheep, pigs, horses, goats, etc.), lab animals (rats, mice, monkeys, etc.), and primates (chimpanzees, humans, gorillas). The language "in combination with" a known composition is intended to include simultaneous administration of the composition of the invention and the known composition, administration of the composition of the invention first, followed by the known composition and administration of the known composition first, followed by the composition of the invention. Any of the therapeutically composition known in the art for treating tetracycline responsive states can be used in the methods of the invention.

The substituted tetracycline compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration (including intraperitoneal, subcutaneous, intravenous, intradermal or intramuscular injection), solutions of a substituted tetracycline compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Substituted tetracycline compounds may be formulated in sterile form in multiple or single dose formats such as being dispersed in a fluid carrier such as sterile physiological saline or 5% saline dextrose solutions commonly used with injectables.

Additionally, it is also possible to administer the substituted tetracycline compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats. Also, the compounds of the invention may be used to treat non-animal subjects, such as plants.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule.

It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

EXEMPLIFICATION OF THE INVENTION

The following example illustrates various methods of synthesizing 9- and 7-substituted tetracycline compounds in accordance with the invention. Other compounds of the invention can be synthesized using methods described herein and/or methods known in the art.

Example 1

Synthesis of 9-Amino-Substituted Tetracycline Compounds

To an ice cold solution of doxycycline (2 g, 4.15 mmol) in 30 ml of concentrated $H_2SO_4$, potassium nitrate (0.5 g; 1.2 eq) was added portion-wise. The reaction mixture was stirred for 1½ hours. The acid solution was then added to 200 ml of ice water. The precipitated yellow material was filtered. The filtered material was dissolved in methanol. After the methanol was evaporated, the product was extracted with n-butanol. The organic phase was washed with saturated $NaHCO_3$ twice and the solvent removed in vacuo.

The resulting product was dissolved in 50 ml of methanol and 1 ml of concentrated HCl and hydrogenated on Pd/C to yield the 9- and 7-aminodoxycycline positional isomers as an off-yellow solid. The isomers can be purified by HPLC and other techniques known in the art.
9-Aminodoxycycline
(9-amino-6-α-deoxy-5-hydroxytetracyline)
MS(M+H):460 $^1$HNMR ($CD_3OD$): δ 7.62 (d, 1H, H-8); 7.14 (d, 1H, H-7); 4.42 (s, 1H, H-4); 3.6 (dd, 1H, H-5); 2.98, 2.90 (each s, each 3H, $NMe_2$); 2.84(d, 1H, H-4a); 2.72 (m, 1H, H-6); 2.59 (dd, 1H, H-5a); 1.51 (d, 3H, $CH_3$—$C_6$).
General Synthesis of mixed urea of 9- or 7-Amino-6-α-tetracycline compound:

In one portion, 1.2 equivalents of an isocyanate was added to a solution of 9-amino tetracycline compound in DMF and two equivalents of diisoproplyethylamine. The reaction mixture was stirred at room temperature for several hours (usually 4 hours to overnight). The desired product was isolated by C18 reverse-phase column chromatography. The 7-amino tetracycline compound urea can be synthesized using the similar methodology with the 7-amino tetracycline compound as the starting material.

The following compounds were made using the above procedure.
Compound B: 9-Aminonaphthyl Doxycycline urea
(1-Napthyl, 9-amino-6-α-deoxy-5-hydroxy-tetracycline mixed urea)
HNMR ($CD_3OD$): δ 7.9 (d, 1H, H-8); 7.8–7.4 (m, 7H, aryl); 6.9 (bd, 1H, H-7); 4.42 (s, 1H, H-4); 3.6 (d, 1H, H-5); 2.88, 2.77 (each s, each 3H, $NMe_2$); 2.84 (d, 1H, H-4a); 2.72 (m, 1H, H-6); 2.59 (dd, 1H, H-5a); 1.31 (d, 3H, $CH_3$—$C_6$). MS(M+H): calc. 629.63; Found 629.16.
Compound E: 9-Aminophenyl Doxycycline urea
(Phenyl, 9-amino-α-deoxy-5-hydroxy-tetracycline mixed urea)
$^1$HNMR ($CD_3OD$): δ 8.25 (d, 1H, H-8); 7.45 (d, 2H, aryl); 7.29 (m, 2H, aryl); 7.0 (d, 1H, aryl); 6.9 (d, 1H, H-7); 4.25 (s, 1H, H-4); 3.6 (dd, 1H, H-5); 2.85 (bs, 6H, $NMe_2$); 2.84 (d, 1H, H-4a); 2.72 (m, 1H, H-6); 2.58 (dd, 1H, H-5a); 1.54 (d, 3H, $CH_3$—$C_6$). MS(M+H): calc. 579.57; Found 579.15.

Compound F: 9-Amino-t-butyl Doxycycline urea
(Tert-butyl, 9-amino-6-α-deoxy-5-hydroxy-tetracycline mixed urea)
$^1$HNMR (CD$_3$OD); δ 8.1 (d, 1H, H-8); 6.84 (d, 1H, H-7); 4.31 (s, 1H, H-4); 3.55 (dd, 1H, H-5); 2.91 (bs, 6H, NMe$_2$); 2.71–2.57 (m, 3H, H-4a, H-6, H-5a); 1.51 (d, 3H, CH$_3$—C$_6$); 1.36 (s, 9H, tert butyl); MS(M+H): calc. 559.58; Found: 559.19.

Compound I: 9-(4'-Chloro, 2'-trifluoromethylphenyl amino)-Doxycycline urea
4-Chloro, 2-trifluoromethylphenyl, 9-amino-6-α-deoxy-5-hydroxy-tetracycline mixed urea $^1$HNMR (CD$_3$OD): δ 8.28 (d, 1H, H-8); 7.89 (d, 1H, aryl); 7.66 (s, 1H, aryl); 7.58 (d, 1H, aryl); 6.93 (d, 1H, H-7); 4.42 (s, 1H, H-4); 3.56 (dd, 1H, H-5); 2.98 & 2.90 (each s, 3H, NMe$_2$); 2,84 (d, 2H, H-4a); 2.72 (m, 1H, H-6); 2.56 (dd, 1H, H-5a); 1.52 (d, 3H, CH$_3$—C$_6$).MS(M+H): calc.

Compound AJ: 9-(3,5-Bis (trifluoromethylphenyl) amino) Doxycycline urea
(3,5-bis (trifluoromethyl phenyl), 9-amino-6-α-deoxy-5-hydroxy-tetracycline mixed urea)

General Synthesis of Carbamates of 9- or 7-amino-doxycycline:
In a single portion, 1.2 equivalents of chloroformate was added to a solution of 9-aminodoxycycline in DMF in the presence of two equivalent of diisopropylethylamine. The reaction mixture was stirred at room temperature for several hours. The desired product was isolated by C18 reverse-phase column chromatography. The 7-amino tetracycline compound carbamate can be synthesized using the similar methodology with the 7-amino tetracycline compound as the starting material. The following carbamates were synthesized using the general synthesis outlined above.

Compound A: FMOC-9-Amino Doxycycline
(N-Fluorenylmethyloxycarbonyl 9-amino-6-α-deoxy-5-hydroxy-tetracycline)
$^1$HNMR (CD$_3$OD) δ 7.9 (bd, 1H, H-8), 7.69 (d, 2H, aryl); 7.56 (m, 2H, aryl); 7.29 (m, 4H, aryl); 6.8 (d, 1H, H-7); 4.35 (d, 2H, CH$_2$) 4.30 (s, 1H, H-4); 4.15 (m, 1H, CH); 3.5 (dd, 1H, H-5); 2.85 (bd, 6H, NMe$_2$); 2.83 (d, 1H, H-4a); 2.73 (m, 1H, H-6a); 2.57 (dd, 1H, H-5a); 1.40 (d, 3H, CH$_3$—C$_6$). MS(M+H): calc. 682.69; Found: 682.

Compound K: 9-(Fluorophenyl) Doxycycline Carbamate
(N-p-Fluorophenyloxycarbonyl 9-amino-6-α-deoxy-5-hydroxy tetracycline)
$^1$HNMR (CD$_3$OD) δ 7.92 (d, 1H, H-8); 7.11–6.98 (m, 4H, aryl); 6.85 (d, 1H, H-7); 4.34 (s, 1H, H-4); 3.42 (dd, 1H, H-5); 2.86 (bd, 6H, NMe$_2$); 2.83 (d, 1H, H-5a); 2.72 (m, 1H, H-6); 2.56 (dd, 1H, H-5a); 1.43 (d, 3H, CH$_3$—C$_6$). MS(M+H): calc. 598.55; Found: 598.50

Compound L: 9-(4-Methoxyphenyl) Doxycycline Carbamate
(N-p-methoxyphenyloxycarbonyl 9-amino-6-α-deoxy-5-hydroxy tetracycline)
$^1$HNMR (CD$_3$OD): δ 7.92 (bd, 1H, H-8); 6.97 (d, 2H, aryl); 6.82 (m, 3H, H-7 and aryl); 4.36 (s, 1H, H-4); 3.66 (s, 3H, OMe); 3.4 (d, 1H, H-5); 2.86 (bd, 6H, NMe$_2$); 2.83 (d, 1H, H-4a); 2.78 (m, 1H, H-6); 2.56 (dd, 1H, H-5a); 1.43 (d, 3H, CH$_3$—C$_6$). MS(M+H): calc. 610.58; Found: 610.50.

Compound M: 9-BOC-Amino Doxycycline
(N-tert-butyloxycarbonyl 9-amino-6-α-deoxy-5-hydroxy-tetracycline)
$^1$HNMR (CD$_3$OD): δ 8.04 (d, 1H, H-8); 6.92 (d, 1H, H-7); 4.05 (s, 1H, H-4); 3.62 (dd, 1H, H-5); 2.82 (bs, 6H, NMe$_2$); 2.83 (d, 1H, H-4a); 2.74 (m, 1H, H-6); 2.57 (dd, 1H, H-5a); 1.52 (bs, 12H, CH$_3$—C$_6$+tert-butyl); MS(M+H): calc. 560.57; found: 560.16.

Compound AP: 9-Neopentyl Minocycline Carbamate
(N-neopentyloxycarbonyl 9-amino-6-α-deoxy-5-hydroxy-tetracycline)
$^1$HNMR (CD$_3$OD): δ 7.9 (d, 1H, H-8); 6.9 (d, 1H, H-7); 4.36 (s, 1H, H-4); 3.77 (s, 2H, neopentyl CH$_2$); 3.6 (dd, 1H, H-5); 2.88, 2.81 (bs, 6H, NMe$_2$); 2.84 (d, 1H, H-4a); 2.72 (m, 1H, H-6); 2.59 (dd, 1H, H-5a); 1.45 (d, 3H, CH$_3$—C$_6$); 0.89 (s, 9H, neopentyl CH$_3$). MS(M+H): calc. 587.63; Found: 587.5.

Synthesis of 2-Aminothiazole Derivatives of Tetracycline Compounds
Fluorenylmethyloxycarbonyl chloride (1.80 g; 5 mmol) was dissolved in 10 ml of ethyl acetate. This solution was added drop-wise to a suspension of potassium thiocyanate (1.2 eq) in 10 ml of ethyl acetate at 0° and under nitrogen atmosphere. The reaction mixture was left stirring overnight. The reaction mixture was then filtered over celite pad to remove residual salts, and the ethyl acetate was removed in vacuo. The crude yellow material was used to synthesize the compounds below.

Compound AT: 9-FMOC-amino Doxycycline thiocarboxamide
(3-(Fluorenylmethyloxycarbonyl)-1-(9-amino-6-α-deoxy-5-hydroxy tetracycline)-thio carboxamide)
To 300 mg (0.65 mmol) of 9-amino doxycycline in 3 ml of DMF and in the presence of 227 μl (2 eq) of diisopropylethylamine, was added in one portion of 182 mg of fluorenylmethyloxy-carbonyl isothiocyanate in 1 ml of DMF. The reaction mixture was stirred at room temperature for 5 hours. The desired product was isolated through C18 reverse-phase column chromatography.
$^1$HNMR (CD$_3$OD): δ 8.82 (d, 1H, H-8); 7.82 (d, 2H, aryl); 7.72 (d, 2H, aryl); 7.4 (m, 4H, aryl); 6.92 (d, 1H, H-7); 4.56 (d, 2H, CH$_2$); 4.44 (s, 1, H-4); 4.30 (m, 1H, CH); 3.6 (dd, 1H, H-5); 2.98 (bd, 6H, NMe$_2$); 2.84 (d, 1H, H-4a); 2.73 (m, 1H, H-6); 2.56 (dd, 1H, H-5a); 1.54 (d, 3H, CH$_3$—C$_6$). MS(M+H): calc. 741.78; Found: 741.28.

6-α-deoxy-5-hydroxy-tetracycline thiourea
300 mg (0.405 mmol) of 3-(fluorenylmethyloxycarbonyl)-1-(9-amino-6-α-deoxy-5-hydroxy tetracycline)-thio carboxamide was deblocked in a solution of 2% piperidine, 2% DBU in DMF at room temperature. The solvent was then evaporated in vacuo after acidification with concentrated HCl. The residue was dissolved in 1 ml of MeOH and added dropwise to 100 ml of cold ethyl acetate. The precipitated yellow solid was filtered and dried.
$^1$HNMR (CD$_3$OD); δ 7.90 (d, 1H, H-8); 6.95 (d, 1H, H-7); 4.48 (s, 1H, H-4); 3.57 (dd, 1H, H-5); 3.04, 2.92 (two s, each 3H, NMe$_2$); 2.84 (d, 1H, H-4a); 2.7 (m, 1H, H-6); 2.6 (dd, 1H, H-5a); 1.54 (d, 3H, CH$_3$—C$_6$). MS(M+H): calc. 519.54; Found: 519.20.

General Synthesis of 7- or 9-(2'-thiazolyl amino) Tetracycline Compounds
In one portion, the appropriate ax-bromo ketone was added to a tetracycline compound thiourea in a mixture of DMF/Dioxane (3:1) and an equivalent amount of diisopropylethylamine. The reaction mixture was left stirring overnight. The thiazole product was isolated through C18 reverse-phase column chromatography. The following thiazole compounds were synthesized using the method described above.

Compound N: 9-(4'-Phenyl thiazolyl)-amino Doxycycline
2 [9 (amino-6-α-deoxy-5-hydroxy tetracycline)]-4-phenyl thiazole:
$^1$HNMR (CD$_3$OD): δ 8.25 (d, 1H, H-8); 7.8 (d, 2H, aryl); 7.45 (m, 3H, aryl); 7.1 (s, 1H, vinyl); 7.09 (d, 1H, H-7); 4.46

(s, 1H, H-4); 3.6 (dd, 1H, H-5); 2.91 & 2.88 (Two s, each 3H, NMe$_2$); 2.84 (d, 1H, H-4a); 2.7 (m, 1H, H-6); 2.57 (dd, 1H, H-5a); 1.6 (d, 3H, CH$_3$—C$_6$). MS(M+H): calc. 619.66; Found: 619.19.

Compound O: 9-(4'-Ethyl thiazolyl)-amino Doxycycline
2 [9-(amino-6-α-deoxy-5-hydroxy tetracycline)-4-ethyl] thiazole $^1$HNMR (CD$_3$OD): δ 7.9 (d, 1H, H-8); 7.05 (d, 1H, H-7); 6.55 (s, 1H, vinyl); 4.46 (s, 1H, H-4); 3.57 (dd, 1H, H-5a); 2.96 (bs, 6H, NMe$_2$), 2.87 (d, 1H, H-4a); 2.7 (m, 1H, H-6); 2.6 (m, 3H, H-5a and CH$_2$ of the ethyl); 1.59 (d, 3H, CH$_3$—C$_6$); 1.28 (d, 3H, CH$_3$ of the ethyl); MS(M+H): calc. 571.62; Found: 571.2.

Compound Q: 9-(4-Methoxyphenylthiazolyl)-amino Doxycycline
(2 [(9-amino-6-α-deoxy-5-hydroxy tetracycline)]-4-(4-methoxyphenyl) thiazole)

$^1$HNMR (CD$_3$OD): δ 7.94 (d, 1H, H-8); 7.68 (d, 2H, aryl); 7.10 (d, 1H, H-7); 7.06 (d, 2H, aryl; 4.49 (s, 1H. H-4); 3.86 (s, 3H, OMe); 3.56 (dd, 1H, H-5); 3.0 & 2.94 (two s, each 3H, NMe$_2$); 2.87 (d, 1H, H-4a); 2.73 (m, 1H, H-6); 1.63 (d, 3H, CH$_3$—C$_6$). MS(M+H): calc. 649.68; Found: 649.15.

Compound R: 9-(3-Nitrophenylthiazolyl)-amino Doxycycline
(2 [9-(amino-6-α-deoxy-5-hydroxy tetracycline)]-4-(3-nitrophenyl) thiazole)

$^1$HNMR (CD$_3$OD): δ 8.6 (m, 2H, aryl); 8.2 (d, 1H, H-8); 8.1 (d, 1H, aryl); 7.6 (m, 1H, aryl); 7.3 (s, 1H, vinyl); 6.9 (d, 1H, H-7); 4.44 (s, 1H, H-4); 3.57 (dd, 1H, H-5); 3.0 & 2.91 (two s, each 3H, NMe$_2$); 2.84 (s, 1H, H-4a); 2.7 (m, 1H, H-6); 2.57 (dd, 1H, H-5a); 1.56 (d, 3H, CH$_3$—C$_6$). MS(M+H): calc. 664.66; Found: 664.60.

Compound S: 9-(4-Methyl-5-phenylthiazolyl)-amino Doxycycline
(2 [9(amino-6-α-deoxy-5-hydroxy tetracycline)]-4-phenyl-5-methyl thiazole)

$^1$HNMR (CD$_3$OD): δ 7.98 (d, 1H, H-8); 7.6–7.4 (m, 5H, aryl); 7.05 (d, 1H, H-7); 4.46 (s, 1H, H-4); 3.57 (dd, 1H, H-5); 2.95 (bs, 6H, NMe$_2$); 2.87 (d, 1H, H-4a); 2.7 (m, 1H, H-6); 2.6 (dd, 1H, H-5a); 2.36 (s, 3H, CH$_3$): 1.57 (d, 3H, CH$_3$—C$_6$). MS(M+H): calc. 633.68; Found: 633. 61.

Compound U: (9-(N,N-Dimethyl Glycyl)-Doxycycline)
NN-Dimethylglycine (1.2 mmol) is dissolved in DMF (5 mL) and O-Benzotriazol-1-yl-N,N,N',N',-tetramethyluronium hexafluorophosphate (HBTU, 1.2 mmol) is added. The solution is then stirred for 5 minutes at room temperature. To this solution, 9-amino doxycycline (1 mmol) is added, followed by the addition of diisopropylethyl amine (DIEA, 1.2 mmol). The reaction is then stirred at room temperature for 2 hours. The solvent, DMF, is removed under vaccum. The crude material is dissolved in 5 mL of MeOH and filtered using autovials and purified using preparative HPLC. The structure of the product is characterized using 1H NMR, HPLC, and MS.

Example 2

In Vitro Minimum Inhibitory Concentration (MIC) Assay

The following assay was used to determine the efficacy of tetracycline compounds against common bacteria (*E. coli, S. aureus, E. hirae*, and *E. faecalis*). 2 mg of each compound was dissolved in 100 μl of DMSO. The solution was then added to cation-adjusted Mueller Hinton broth (CAMHB), which resulted in a final compound concentration of 200 μg per ml. The tetracycline compound solutions were diluted to 50 μL volumes, with a test compound concentration of 0.098 μg/ml. Optical density (OD) determinations were made from fresh log-phase broth cultures of the test strains. Dilutions were made to achieve a final cell density of about 5×10$^5$ CFU/ml.

50 μl of the cell suspensions were added to each well of the microtiter plates. The final cell density was approximately 5×10$^5$ CFU/ml. These plates were incubated at 35° C. in an ambient air incubator for approximately 18 hr.

The plates were read with a microplate reader and were visually inspected when necessary. The MIC is defined as the lowest concentration of the tetracycline compound that inhibits growth. In Table 2, * indicates good inhibition of the growth of a particular organism,  indicates inhibition of growth at a lower concentration, and * indicates very good inhibition of growth. Certain substituted tetracycline compounds of the invention had MIC's less than about 10 μg/ml. Other substituted tetracycline compounds of the invention had MIC's of less than about 5 μg/mL, and still other compounds had MIC's less than about 1 μg/mL.

TABLE 2

| ID | STRUCTURE | NAME | S. aureus | E. hirae | E. coli | E. faecalis |
|---|---|---|---|---|---|---|
| A | 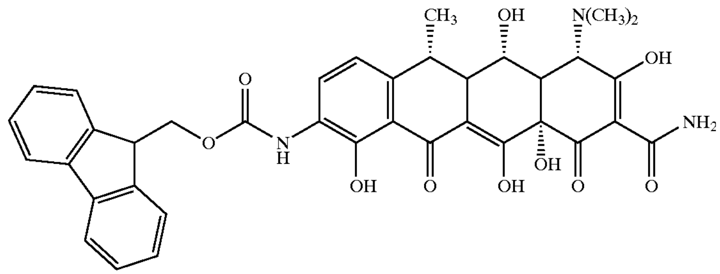 | FMOC-0-amino Doxycycline | * | * | * | *** |
| B | 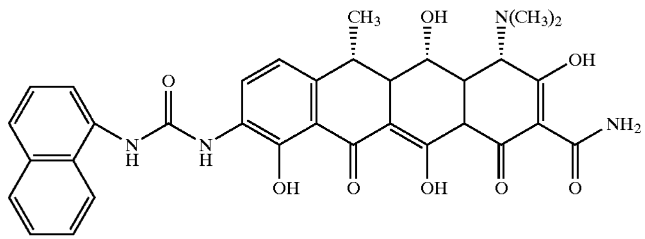 | 9-Naphth-1-yl doxycycline urea |  |  |  | * |
| C | 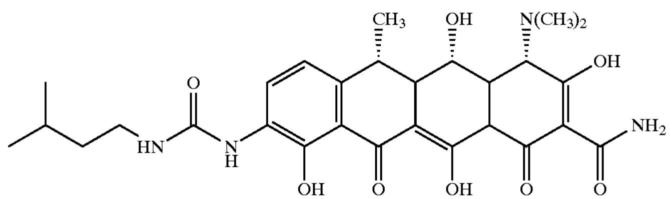 | 9-(3'-methyl butyl) Doxycycline urea |  | NT |  | ** |

TABLE 2-continued

| ID | STRUCTURE | NAME | S. aureus | E. hirae | E. coli | E. faecalis |
|---|---|---|---|---|---|---|
| D | 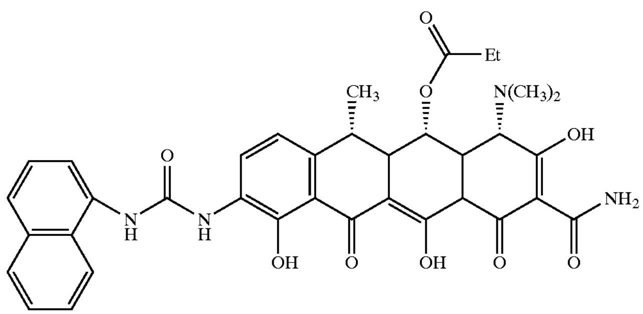 | 9-(Naphth-1-yl) doxycycline urea 5-propionic acid ester |  | NT |  | ** |
| E | 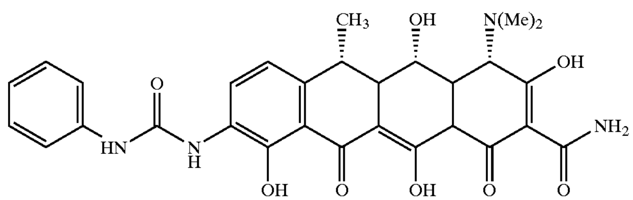 | 9-Phenyl Doxycycline urea | ** | * |  | * |
| F | 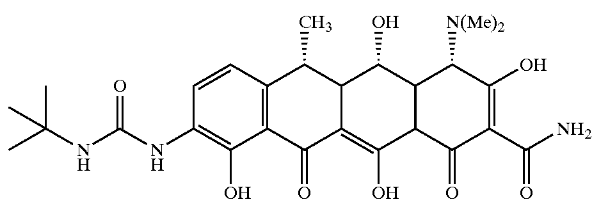 | 9-t-butyl doxycycline urea |  |  | * | ** |
| I | 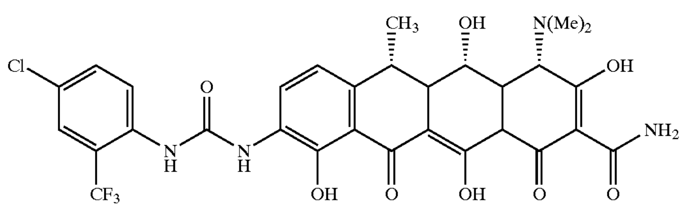 | 9-(4'-chloro-2'-perfluoromethyl)-doxycycline urea |  | NT |  | ** |

TABLE 2-continued

| ID | STRUCTURE | NAME | S. aureus | E. hirae | E. coli | E. faecalis |
|----|-----------|------|-----------|----------|---------|-------------|
| K  | 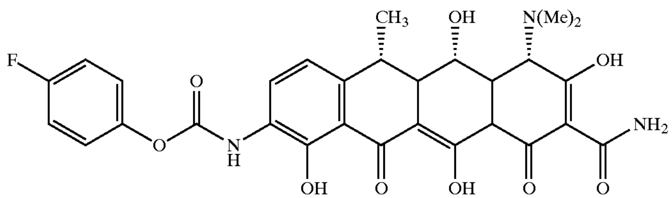          | 9(4'-Fluorophenyl) doxycycline carbamate | * | * | * | * |
| L  | 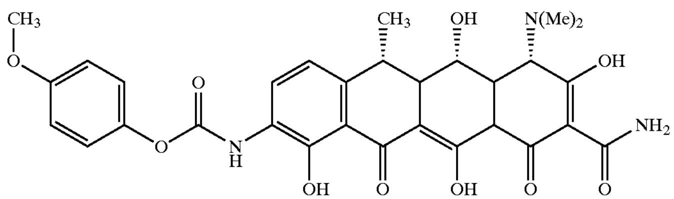          | 9(4'-Methoxyphenyl) doxycycline carbamate | * | * | * | * |
| M  | 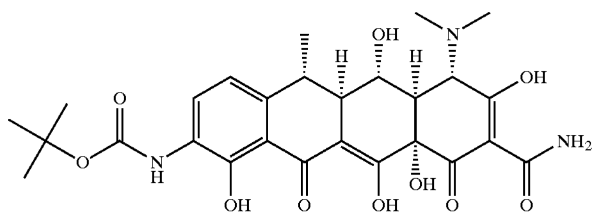          | 9-BOC-amino doxycycline |  |  |  |  |
| N  | 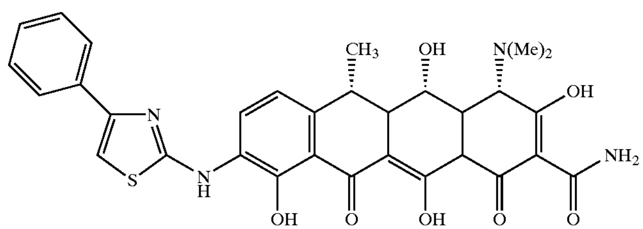          | 9-(phenylthiazolyl)amino doxycycline | *** | NT | * | *** |

TABLE 2-continued

| ID | STRUCTURE | NAME | S. aureus | E. hirae | E. coli | E. faecalis |
|---|---|---|---|---|---|---|
| O | 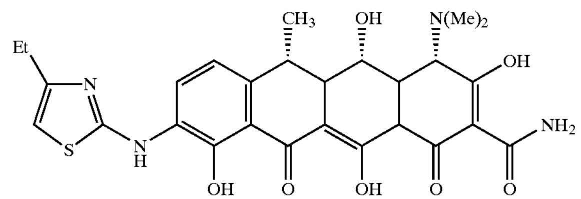 | 9-(ethyl thiazolyl) amino doxycycline | *** | NT | * | ** |
| P | 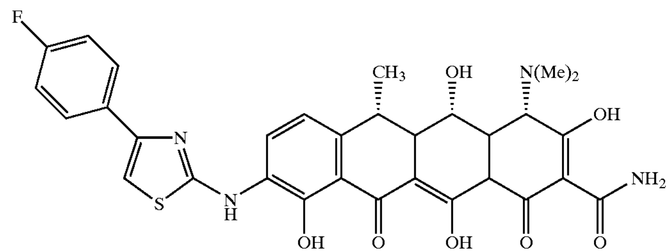 | 9-(4'-Fluorophenylthiazolyl) amino doxycycline | * | NT | * | ** |
| Q | 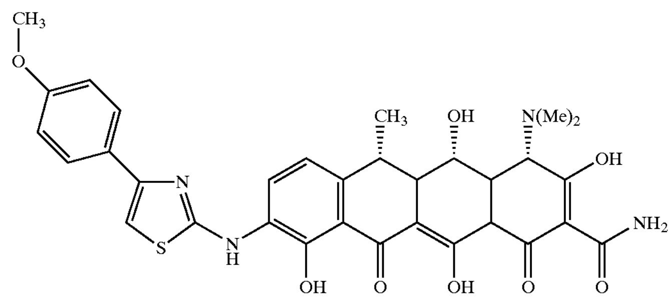 | 9-(4'-Methoxyphenyl thiazolyl)-amino doxycycline | ** | NT | * | ** |
| R | 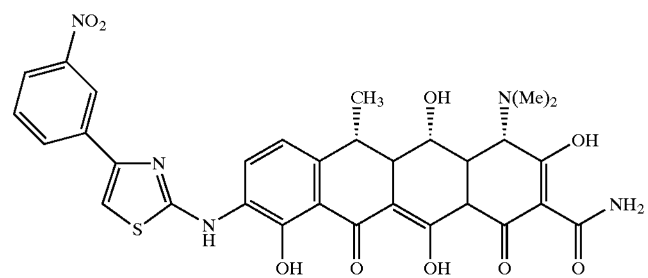 | 9(3'-Nitrophenylthiazolyl)-amino doxycycline | * | * | * | *** |

TABLE 2-continued

| ID | STRUCTURE | NAME | S. aureus | E. hirae | E. coli | E. faecalis |
|----|-----------|------|-----------|----------|---------|-------------|
| S  | 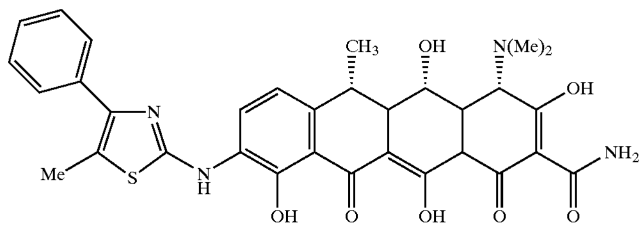          | 9 (4-Methyl, 3-phenylthiazolyl)-amino doxycycline | ** | NT | * | *** |
| T  | 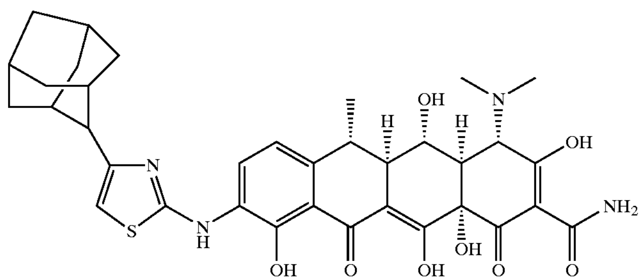          | 9-(Adamantyl thiazolyl) amino-doxycycline | * | * | * |  |
| U  | 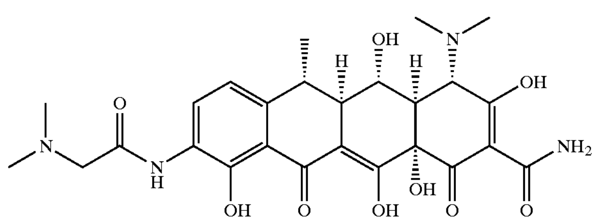          | 9-(N,N-Dimethyl glycyl)-doxycycline | * | * | * | NT |
| V  | 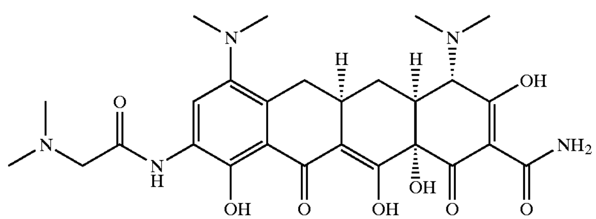          | 9-(N,N-Dimethylamino-glycyl) minocycline | NT | NT | NT | NT |

TABLE 2-continued

| ID | STRUCTURE | NAME | S. aureus | E. hirae | E. coli | E. faecalis |
|---|---|---|---|---|---|---|
| W | 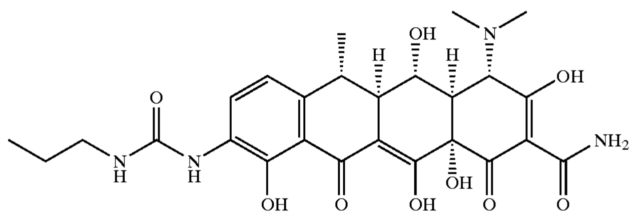 | 9-propyl doxycycline urea | ** | * |  |  |
| X | 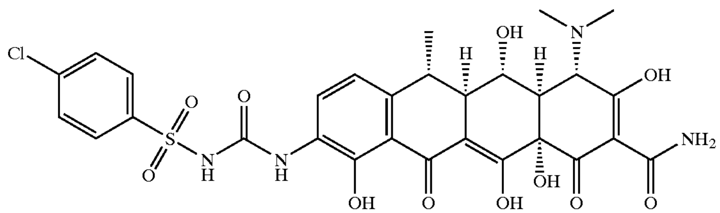 | 9-(4'-chlorophenyl sulfonyl) doxycycline urea | ** | * | * | ** |
| Y | 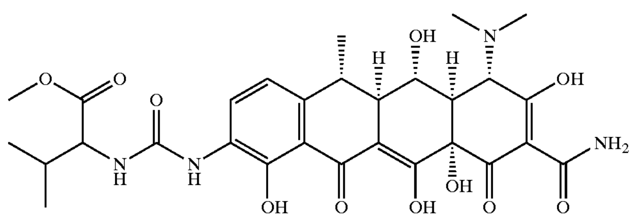 | 9-valine doxycycline urea | * | * | * | * |
| Z | 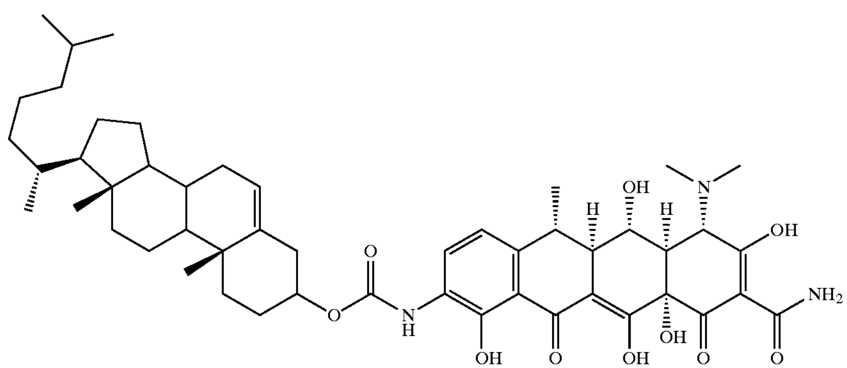 | 9-Cholesterol doxycycline carbamate | * | * | * | * |

TABLE 2-continued
| ID | STRUCTURE | NAME | S. aureus | E. hirae | E. coli | E. faecalis |
|---|---|---|---|---|---|---|
| AA | 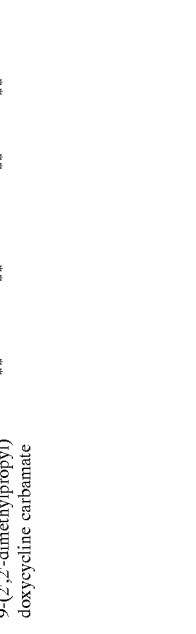 | 9-(2',2'-dimethylpropyl) doxycycline carbamate |  |  |  |  |
| AB | 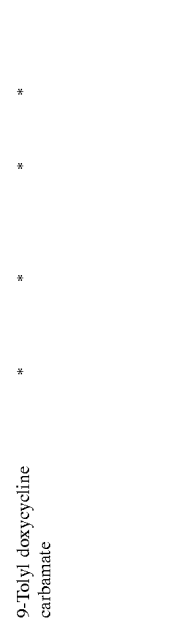 | 9-Tolyl doxycycline carbamate | * | * | * | * |
| AC | 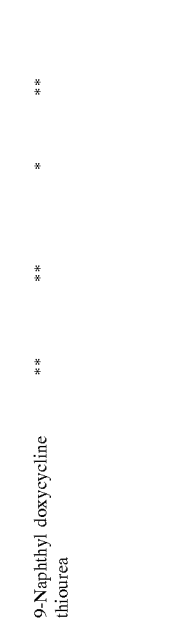 | 9-Naphthyl doxycycline thiourea |  |  | * | ** |
| AD | 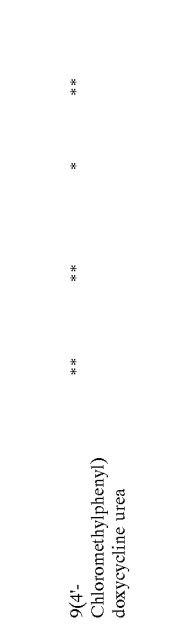 | 9(4'-Chloromethylphenyl) doxycycline urea |  |  | * | ** |

TABLE 2-continued

| ID | STRUCTURE | NAME | S. aureus | E. hirae | E. coli | E. faecalis |
|----|-----------|------|-----------|----------|---------|-------------|
| AE | 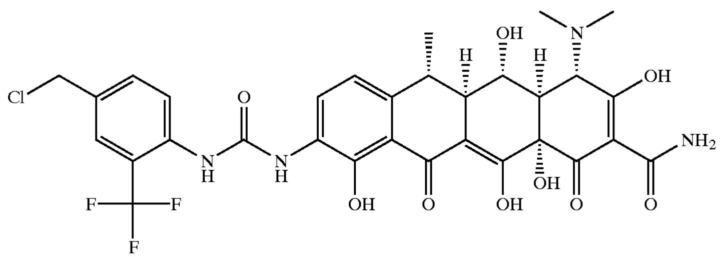 | 9(4'-Chloromethyl, 2'-trifluoromethylphenyl) doxycycline urea |  |  |  |  |
| AF | 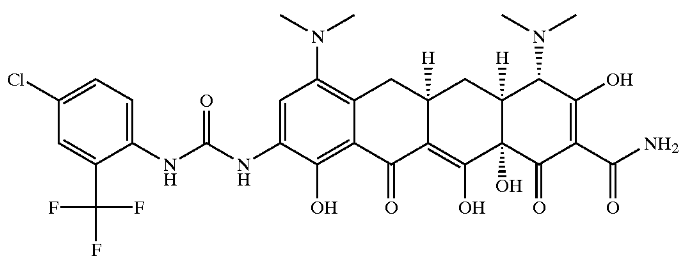 | 9 (4-chloro, 2-trifluoromethylphenyl) minocycline urea |  | * | * | *** |
| AG | 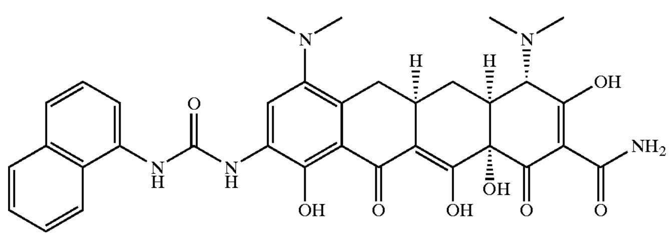 | 9-Naphthyl minocycline urea |  |  |  |  |

TABLE 2-continued

| ID | STRUCTURE | NAME | S. aureus | E. hirae | E. coli | E. faecalis |
|----|-----------|------|-----------|----------|---------|-------------|
| AH | 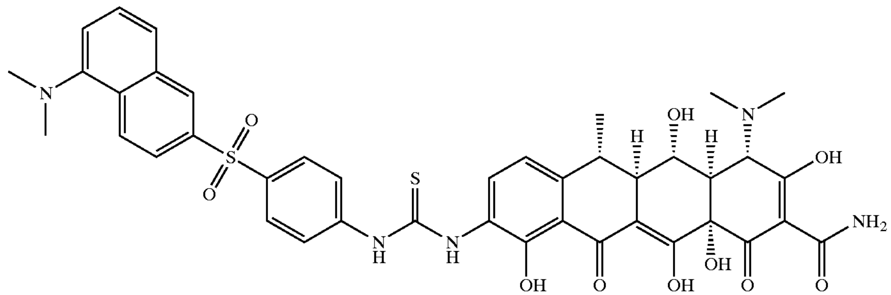 | 9-Dansyl-phenyl doxycycline thiourea | * | * | * | * |
| AI | 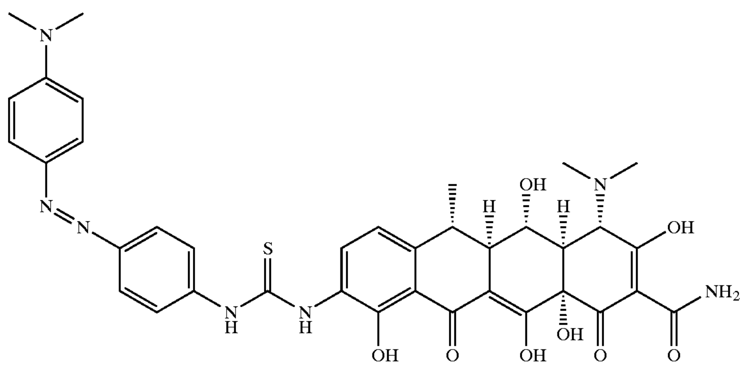 | 9-DABF-phenyl doxycycline thiourea |  | * | * | *** |
| AJ | 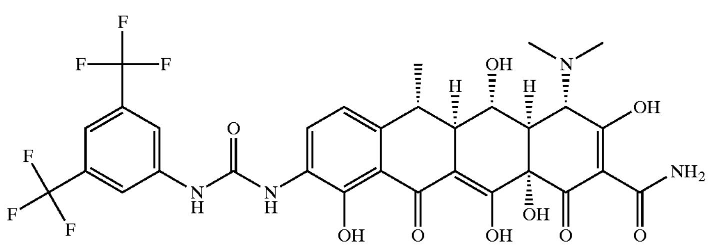 | 9(3,5-Bis(trifluoromethyl)phenyl doxycycline urea | * | * | * | * |

TABLE 2-continued

| ID | STRUCTURE | NAME | S. aureus | E. hirae | E. coli | E. faecalis |
|----|-----------|------|-----------|----------|---------|-------------|
| AK | 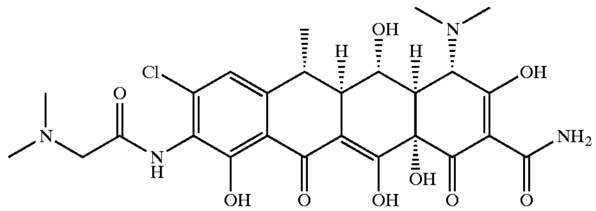 | 8-Chloro-9-N,N-Dimethylamino glycyl doxycycline | * | * | * | * |
| AL | 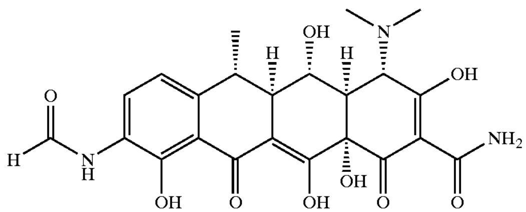 | 9-Forylamino doxycycline | ** | * |  | * |
| AM | 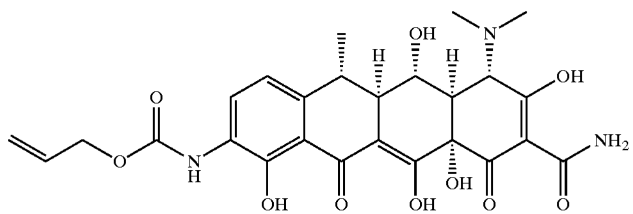 | 9-Propenyl doxycycline carbamate | * | * |  | * |
| AN | 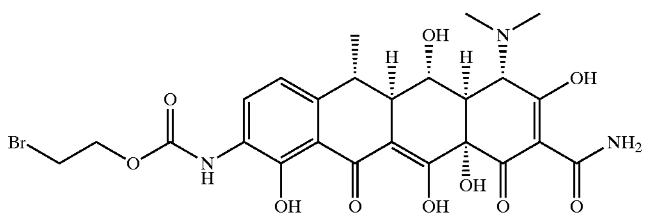 | 9-Bromoethyl doxyglycine carbamate |  |  |  | * |

TABLE 2-continued

| ID | STRUCTURE | NAME | S. aureus | E. hirae | E. coli | E. faecalis |
|----|-----------|------|-----------|----------|---------|-------------|
| AO | 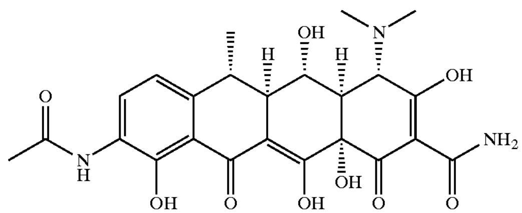 | 9-Acetamide doxycycline | * | * | * | ** |
| AP | 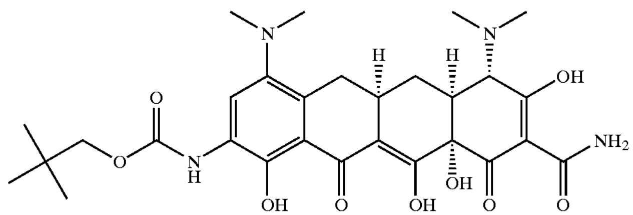 | 9-(2',2'-dimethyl propyl) minocycline carbamate |  |  | * | ** |
| AQ | 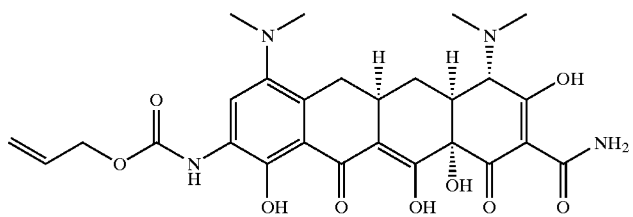 | 9-Isopropenyl minocycline carbamate | * | * | * | * |
| AR | 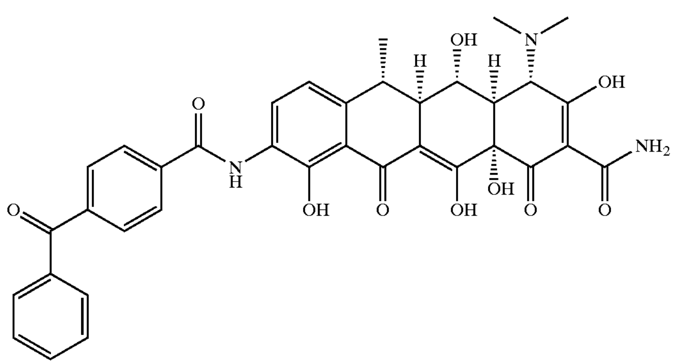 | 9-(4-Benzoylbenzoyl)amino doxycycline |  |  | * | ** |

TABLE 2-continued
| ID | STRUCTURE | NAME | S. aureus | E. hirae | E. coli | E. faecalis |
|----|-----------|------|-----------|----------|---------|-------------|
| AS | 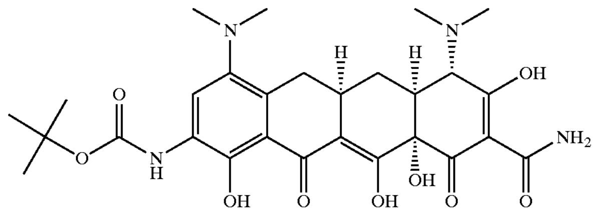 | 9-BOC-amino minocycline |  |  | * | ** |
| AT | 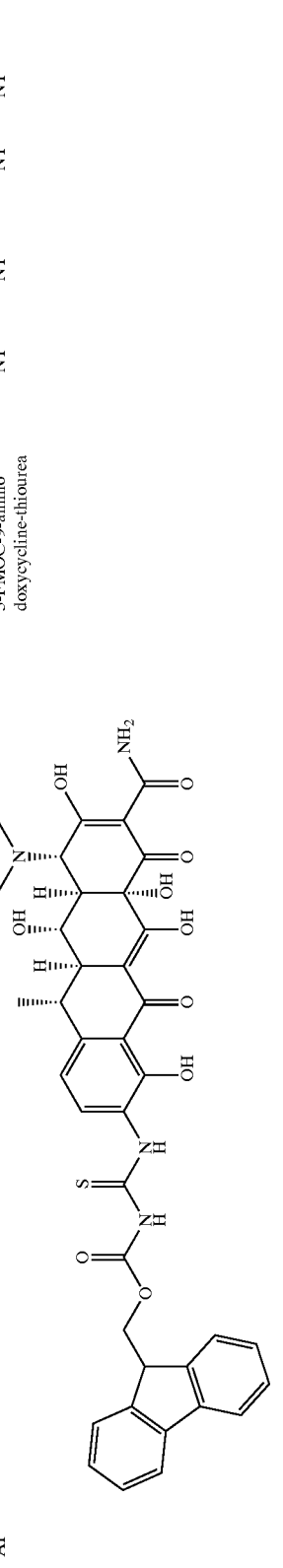 | 3-FMOC-9-amino doxycycline-thiourea | NT | NT | NT | NT |
| AU | 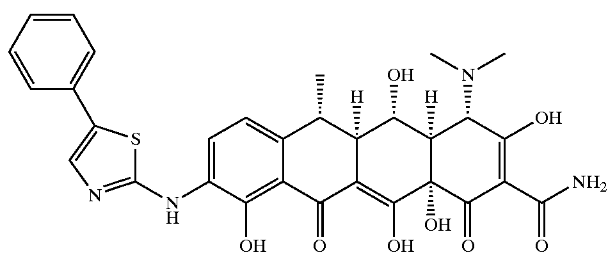 | 9-(Phenylthiazolyl)amino doxycycline | * |  | * | ** |

TABLE 2-continued

| ID | STRUCTURE | NAME | S. aureus | E. hirae | E. coli | E. faecalis |
|---|---|---|---|---|---|---|
| AV | 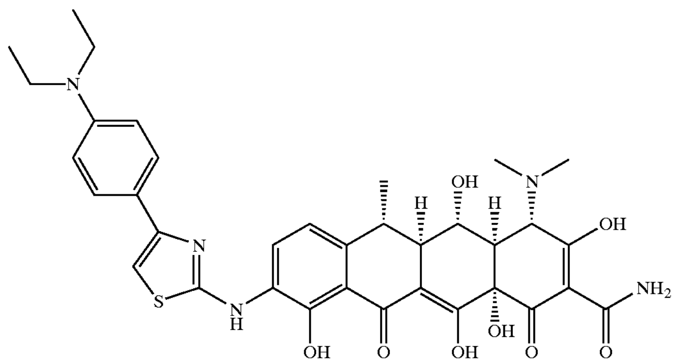 | 9(4-Diethylaminophenyl thiazolyl)-amino doxycycline | * | NT | * | * |
| AW | 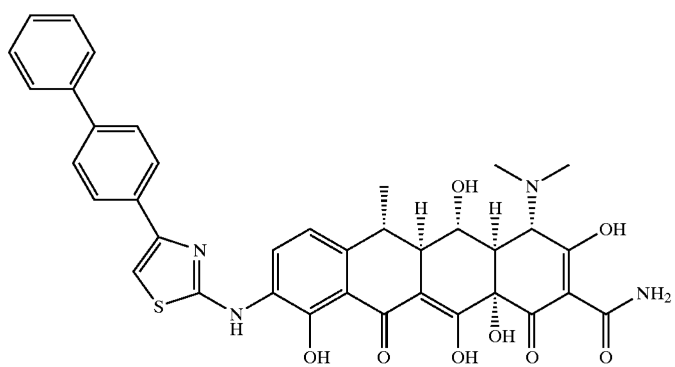 | 9(Biphenylthiazolyl) amino-doxycycline | * | * | * | * |

TABLE 2-continued

| ID | STRUCTURE | NAME | S. aureus | E. hirae | E. coli | E. faecalis |
|----|-----------|------|-----------|----------|---------|-------------|
| AX | 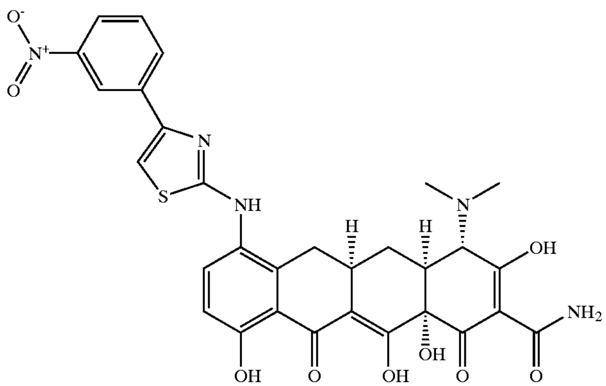 | 7-(3-Nitrophenylthiazolyl) amino sancycline |  | * | * | *** |
| AY | 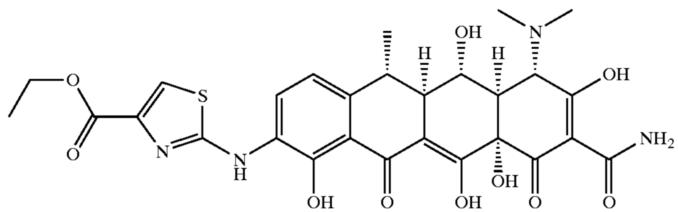 | 9-(Ethoxycarbonylthiazolyl) amino doxycycline |  |  | * | * |
| AZ | 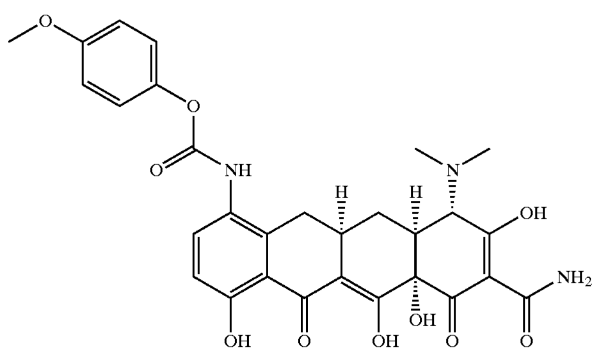 | 7-(4-Methoxyphenyl) sancycline carbamate |  |  | * | ** |

TABLE 2-continued

| ID | STRUCTURE | NAME | S. aureus | E. hirae | E. coli | E. faecalis |
|----|-----------|------|-----------|----------|---------|-------------|
| BA | 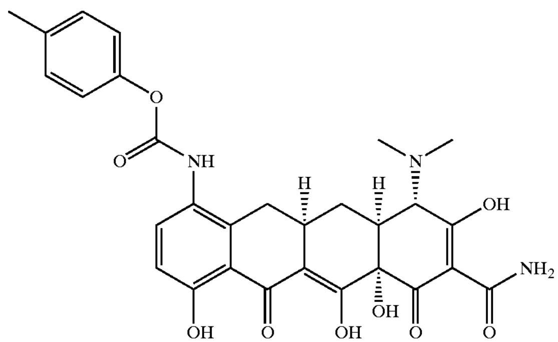 | 7-(4'-Methylphenyl Sancycline Carbamate | * | * | * | ** |
| BB | 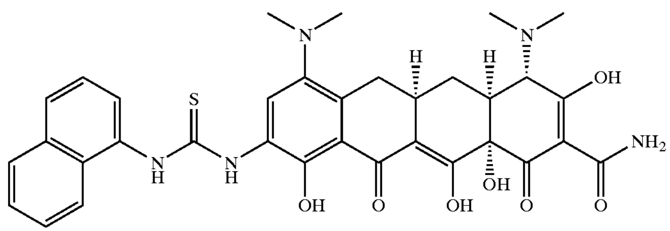 | 9-(Naphth-1-yl) minocycline thiourea |  |  | * | ** |
| BC | 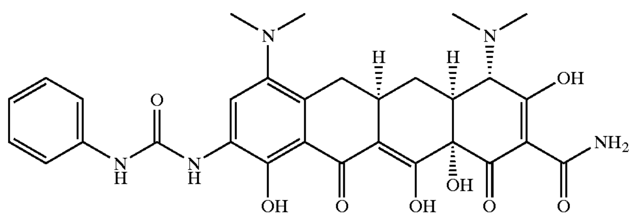 | 9-(Phenyl) minocycline urea |  |  |  |  |
| BD | 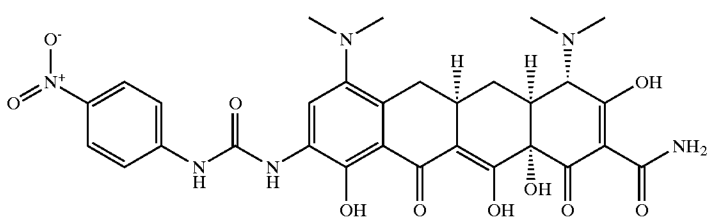 | 9-(4'-phenyl) minocycline urea |  |  | * | ** |

TABLE 2-continued

| ID | STRUCTURE | NAME | S. aureus | E. hirae | E. coli | E. faecalis |
|---|---|---|---|---|---|---|
| BE | 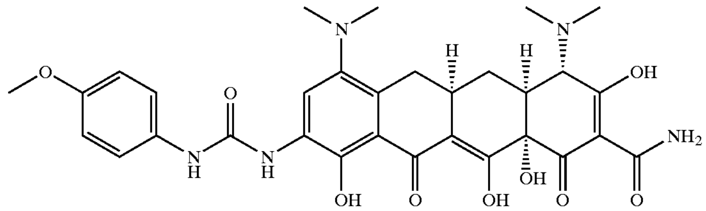 | 9-(4'-methoxyphenyl) minocycline urea | * |  |  | ** |
| BF | 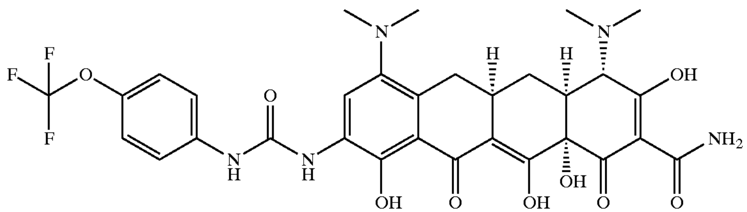 | 9-(4-trifluoromethoxyphenyl) minocycline urea |  |  |  |  |
| BG | 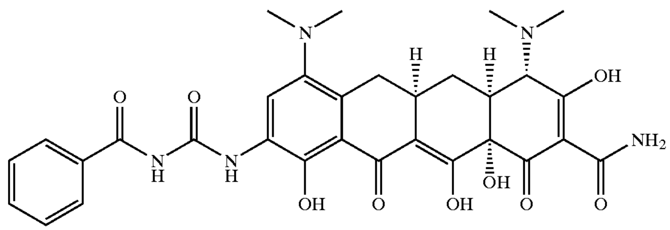 | 9-(Benzoyl) Minocycline urea |  |  | * | ** |
| BH | 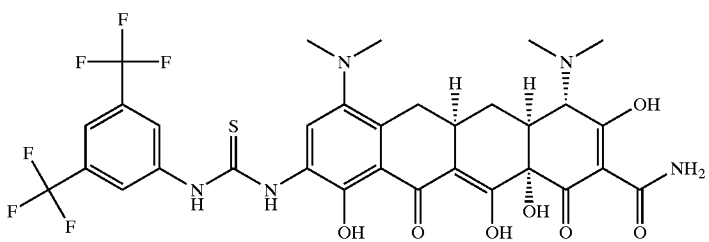 | 9-(2', 5'-diperfluoromethyl phenyl) minocycline thiourea |  |  |  |  |

TABLE 2-continued

| ID | STRUCTURE | NAME | S. aureus | E. hirae | E. coli | E. faecalis |
|----|-----------|------|-----------|----------|---------|-------------|
| BI | 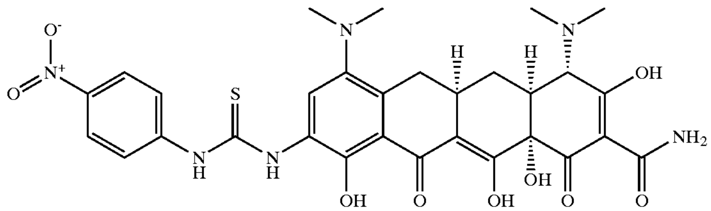 | 9-(4'-Nitrophenyl)-minocycline thiourea |  |  | * | ** |
| BJ | 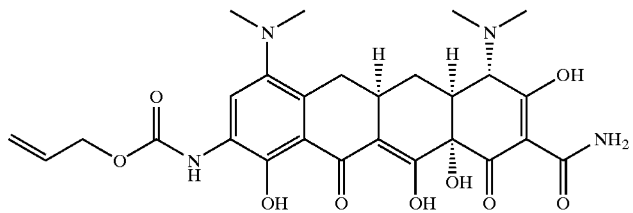 | 9-(prop-2-enyl) minocycline carbamate |  |  | * | ** |
| BK | 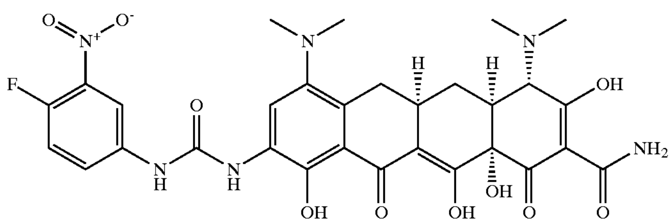 | 9-(4'-Fluoro-3'-nitrophenyl)0minocycline urea |  |  | * | ** |
| BL | 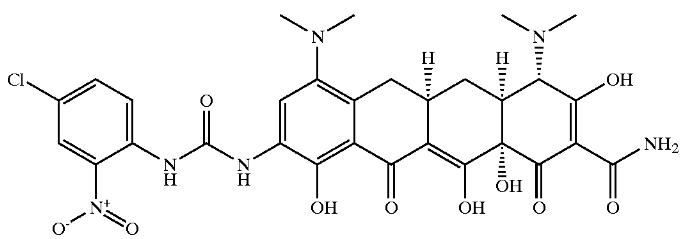 | 9-(4'-Chloro-2'-nitrophenyl)-minocycline urea |  |  |  |  |

TABLE 2-continued

| ID | STRUCTURE | NAME | S. aureus | E. hirae | E. coli | E. faecalis |
|----|-----------|------|-----------|----------|---------|-------------|
| BM | 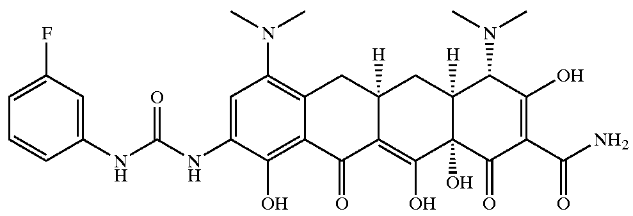 | 9-(3'-Fluorophenyl) minocycline urea |  |  | * | ** |
| BN | 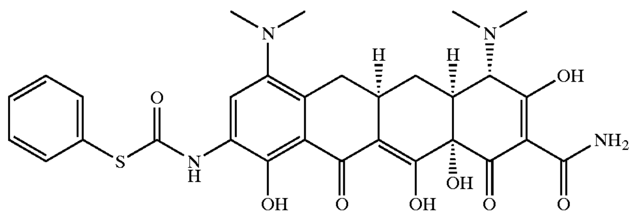 | 9-Phenyl minocycline thiocarbamate | * | * | * | * |
| BO | 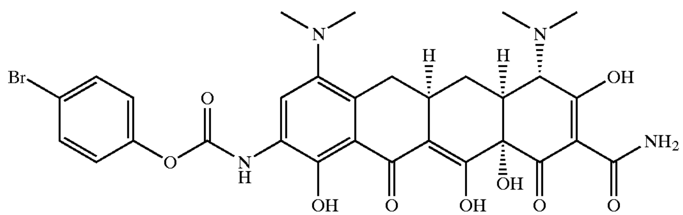 | 9-(4'-Bromophenyl)- minocycline carbamate | * | * | * | * |
| BP | 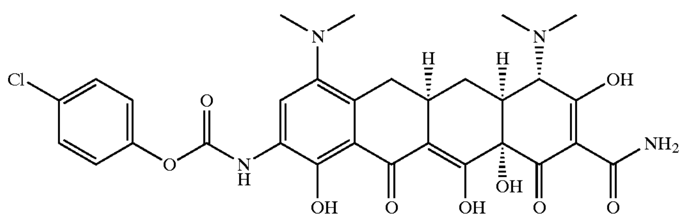 | 9-(4'-Chlorophenyl) minocycline carbamate | * | * | * | * |

TABLE 2-continued

| ID | STRUCTURE | NAME | S. aureus | E. hirae | E. coli | E. faecalis |
|----|-----------|------|-----------|----------|---------|-------------|
| BQ | 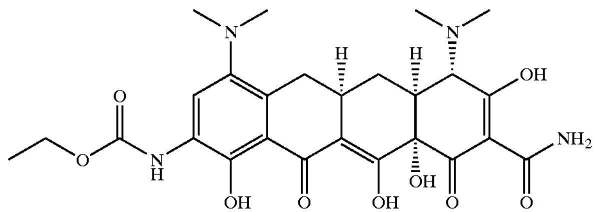 | 9-(Ethyl)-minocycline carbamate | * |  |  |  |
| BR | 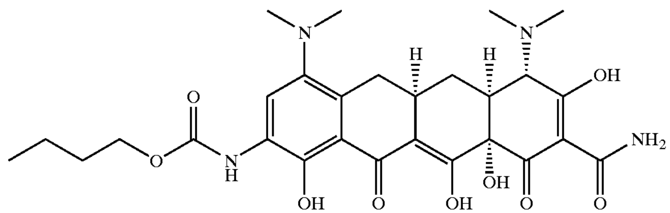 | 9-(n-Butyl)-minocycline carbamate |  |  |  |  |
| BS | 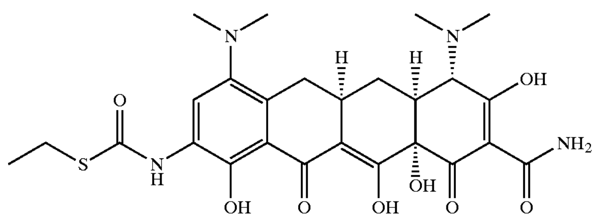 | 9-(Ethyl)-minocycline thiocarbamate |  |  | * | * |
| BT | 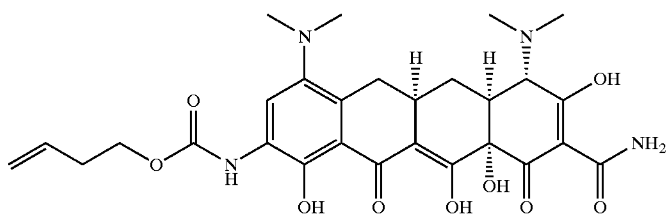 | 9-(But-3-enyl) minocycline carbamate |  |  |  |  |

TABLE 2-continued

| ID | STRUCTURE | NAME | S. aureus | E. hirae | E. coli | E. faecalis |
|----|-----------|------|-----------|----------|---------|-------------|
| BU | 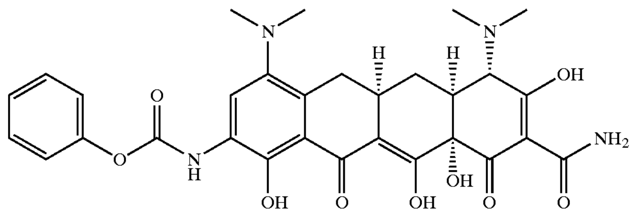 | 9-(Phenyl)-minocycline carbamate | * | * | * | * |
| BV | 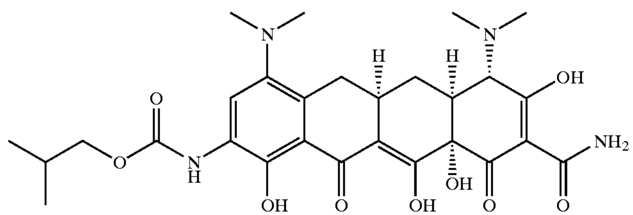 | 9-(Isobutyl)-minocycline carbamate |  |  |  |  |

Equivalents

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

What is claimed is:

1. A substituted tetracycline compound, wherein said compound is of the formula:

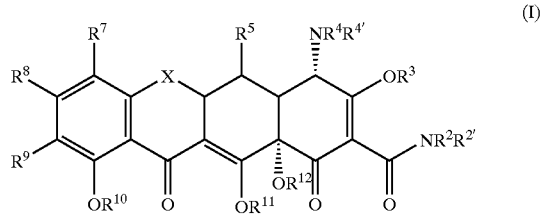

(I)

wherein:

X is CHC($R^{13}$Y'Y), C$R^{6'}R^6$, S, N$R^6$, or O;

$R^2$ is hydrogen, alkyl, alkynyl, alkoxy, alkylthio, alkylsulfinyl, alkylsulfonyl, alkylamino, arylalkyl, aryl, heterocyclic, heteroaromatic or a prodrug moiety;

$R^4$ and $R^{4'}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{2'}$, $R^3$, $R^{10}$, $R^{11}$ and $R^{12}$ are each hydrogen or a pro-drug moiety;

$R^5$ is hydrogen, hydroxyl, or a prodrug moiety;

$R^6$, $R^{6'}$, and $R^8$ are each independently hydrogen, alkyl, alkenyl, alkynyl, aryl, alkoxy, alkylthio, alkylsulfinyl, alkylsulfonyl, alkylamino, arylalkyl, or halogen;

$R^7$ is hydrogen, dialkylamino, or heteroaryl-amino;

$R^{13}$ is hydrogen, hydroxy, alkyl; alkenyl; alkynyl; alkoxy; alkylthio; alkylsulfinyl; alkylsulfonyl; alkylamino; or an arylalkyl;

Y' nd Y are each independently hydrogen; halogen; hydroxyl; cyano, sulfhydryl; amino; alkyl; alkenyl; alkynyl; alkoxy; alkylthio; alkylsulfinyl; alkylsulfonyl; alkylamino; or an arylalkyl;

$R^9$ is hydrogen, or heteroaryl-amino;

and pharmaceutically acceptable salts thereof, provided that $R^9$ is not hydrogen when $R^7$ is hydrogen or dialkylamino.

2. The compound of claim 1, wherein $R^2$, $R^{2'}$, $R^3$, $R^8$, $R^{10}$, $R^{11}$, and $R^{12}$ are each hydrogen.

3. The compound of claim 2, wherein $R^4$ and $R^{4'}$ are each alkyl.

4. The compound of claim 3, wherein $R^4$ and $R^{4'}$ are each alkyl.

5. The compound of claim 4, wherein said compound is a derivative of tetracycline, minocycline, sancycline, doxycycline, chlortetracycline, oxytetracycline, demeclocycline, or methacycline.

6. The compound of claim 4, wherein $R^5$ is hydrogen.

7. The compound of claim 6, wherein X is CH$_2$, and $R^7$ hydrogen.

8. The compound of claim 6, wherein X is CH$_2$, and $R^7$ is N(Me)$_2$.

9. The compound of claim 4, wherein $R^5$ is hydroxyl or a prodrug moiety, and X is CHR$^6$.

10. The compound of claim 9, wherein $R^5$ is hydroxyl and $R^6$ is CH$_3$.

11. The compound of claim 1, wherein $R^9$ is heteroaryl-amino.

12. The compound of claim 11, wherein said heteroaryl is substituted or unsubstituted thioazolyl.

13. The compound of claim 12, wherein said heteroaryl is substituted thioazolyl.

14. The compound of claim 13, wherein said thiazolyl is substituted with a substituted or unsubstituted aryl.

15. The compound of claim 14, wherein said aryl is phenyl.

16. The compound of claim 14, wherein said aryl is substituted with one or more substituents selected from the group consisting of alkyl, alkenyl, alkynyl, aryl, alkoxy, aryloxy, alkylcarbonyl, arylcarbonyl, amido, trifluoromethyl, halogen, nitro, azo, alkyl sulfonyl, and arylsulfonyl.

17. The compound of claim 16, wherein said substituent is nitro.

18. The compound of claim 16, wherein said substituent is alkyl.

19. The compound of claim 18, wherein said alkyl substituent is methyl.

20. The compound of claim 16, wherein said substituent is selected from the group consisting of alkylcarbonyl, arylcarbonyl, alkoxycarbonyl, aryloxycarbonyl, and amido.

21. The compound of claim 20, wherein said substituent is alkoxycarbonyl.

22. The compound of claim 21, wherein said substituent is ethoxycarbonyl.

23. The compound of claim 1, wherein said compound is 9-(Phenylthiazolyl) amino doxycycline.

24. The compound of claim 1, wherein said compound is 9-(Phenylthiazolyl) amino minocycline.

25. The compound of claim 1, wherein said compound is

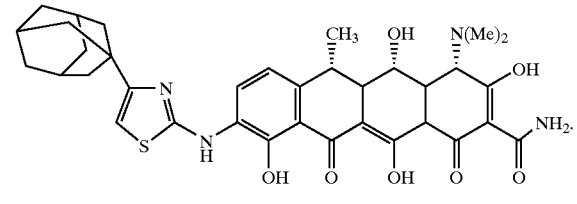

26. The compound of claim 1, wherein said compound is 7-(3'Phenylthiazolyl) amino doxycycline.

27. A method for treating a tetracycline responsive state in a mammal, comprising administering to said mammal a substituted tetracycline compound of formula (I):

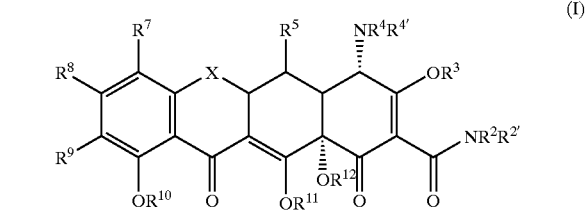

(I)

wherein

X is CHC(R¹³Y'Y), CR⁶'R⁶, S, NR⁶, or O;

R² is hydrogen, alkyl, alkynyl, alkoxy, alkylthio, alkylsulfinyl, alkylsulfonyl, alkylamino, arylalkyl, aryl, heterocyclic, heteroaromatic or a prodrug moiety;

R⁴ and R⁴' are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R²', R³, R¹⁰, R¹¹ and R¹² are each hydrogen or a pro-drug moiety;

R⁵ is hydrogen, hydroxyl, or a prodrug moiety;

R⁶, R⁶', and R⁸ are each independently hydrogen, alkyl, alkenyl, alkynyl, aryl, alkoxy, alkylthio, alkylsulfinyl, alkylsulfonyl, alkylamino, arylalkyl, or halogen;

R⁷ is hydrogen, dialkylamino, or heteroaryl-amino;

R¹³ is hydrogen, hydroxy, alkyl; alkenyl; alkynyl; alkoxy; alkylthio; alkylsulfinyl; alkylsulfonyl; alkylamino; or an arylalkyl;

Y' and Y are each independently hydrogen; halogen; hydroxyl; cyano, sulfhydryl; amino; alkyl; alkenyl; alkynyl; alkoxy; alkylthio; alkylsulfinyl; alkylsulfonyl; alkylamino; or an arylalkyl;

R⁹ is hydrogen, or heteroaryl-amino;

and pharmaceutically acceptable salts thereof, provided that when R⁹ is not hydrogen when R⁷ is hydrogen or dialkylamino.

28. The method of claim 27, wherein said tetracycline responsive state is a bacterial infection.

29. The method of claim 28, wherein said bacterial infection is associated with *E. coli, S. aureus, E. faecalis*, or *E. hirae*.

30. The method of claim 28, wherein said bacterial infection is resistant to unsubstituted tetracycline compounds.

31. The method of claim 27, wherein said tetracycline compound is administered with a pharmaceutically acceptable carrier.

32. A pharmaceutical composition comprising a therapeutically effective amount of a substituted tetracycline compound and a pharmaceutically acceptable carrier, wherein said substituted tetracycline is of the formula:

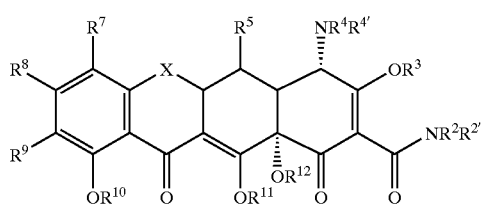
(I)

wherein:

X is CHC(R¹³Y'Y), CR⁶'R⁶, S, NR⁶, or O;

R² is hydrogen, alkyl, alkynyl, alkoxy, alkylthio, alkylsulfinyl, alkylsulfonyl, alkylamino, arylalkyl, aryl, heterocyclic, heteroaromatic or a prodrug moiety;

R⁴ and R⁴' are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R²', R³, R¹⁰, R¹¹ and R¹² are each hydrogen or a pro-drug moiety;

R⁵ is hydrogen, hydroxyl, or a prodrug moiety;

R⁶, R⁶', and R⁸ are each independently hydrogen, alkyl, alkenyl, alkynyl, aryl, alkoxy, alkylthio, alkylsulfinyl, alkylsulfonyl, alkylamino, arylalkyl, or halogen;

R⁷ is hydrogen, dialkylamino, or heteroaryl-amino;

R¹³ is hydrogen, hydroxy, alkyl; alkenyl; alkynyl; alkoxy; alkylthio; alkylsulfinyl; alkylsulfonyl; alkylamino; or an arylalkyl;

Y' and Y are each independently hydrogen; halogen; hydroxyl; cyano, sulfhydryl; amino; alkyl; alkenyl; alkynyl; alkoxy; alkylthio; alkylsulfinyl; alkylsulfonyl; alkylamino; or an arylalkyl;

R⁹ is hydrogen, or heteroaryl-amino;

and pharmaceutically acceptable salts thereof, provided that R⁹ is not hydrogen, when R⁷ is dialkylamino or hydrogen.

33. The pharmaceutical composition of claim 32, wherein said therapeutically effective amount is effective for treatment or prevention of a bacterial infection.

34. A method for synthesizing a 7- or 9-heteroaryl-amino substituted tetracycline compound, comprising:

contacting a tetracycline compound with a nitrating agent, under conditions such that a nitro tetracycline compound is formed;

contacting the nitro tetracycline compound with a hydrogenating agent, under conditions such that an amino tetracycline compound is formed; and contacting the amino tetracycline compound with an amino reactive substrate, such that a 9- or 7-heteroaryl-amine substituted tetracycline compound is formed.

35. The method of claim 34, wherein said substituted tetracycline compound is 9-substituted.

36. The method of claim 34, wherein said substituted tetracycline compound is 7-substituted.

37. The method of claim 34, wherein the nitrating agent is NaNO₂.

38. The method of claim 34, wherein the nitrating agent is contacted with the tetracycline compound under acidic conditions.

39. The method of claim 34, wherein said hydrogenating agent is hydrogen gas.

40. The method of claim 38, wherein said hydrogenating agent further comprises a transition metal catalyst.

41. The method of claim 40, wherein said catalyst is platinum.

42. The method of claim 34, wherein said amino reactive compound is an isocyanate.

43. The method of claim 34, wherein said amino reactive compound is isothiocyanate.

44. The method of claim 34, wherein said amino reactive compound is an unsubstituted or substituted chloroformate.

45. A method for synthesizing a 7- or 9-substituted tetracycline compound of formula (I) comprising contacting a reactive intermediate with appropriate reagents under appropriate conditions, such that a substituted tetracycline compound is formed, wherein formula (I) is:

83

(I)

wherein:

X is CHC($R^{13}$Y'Y), C$R^{6'}R^6$, S, N$R^6$, or O;

$R^2$ is hydrogen, alkyl, alkynyl, alkoxy, alkylthio, alkylsulfinyl, alkylsulfonyl, alkylamino, arylalkyl, aryl, heterocyclic, heteroaromatic or a prodrug moiety;

$R^4$ and $R^{4'}$ are each hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

$R^{2'}$, $R^3$, $R^{10}$, $R^{11}$ and $R^{12}$ are each hydrogen or a pro-drug moiety;

$R^5$ is hydrogen, hydroxyl, or a prodrug moiety;

$R^6$, $R^{6'}$, and $R^8$ are each independently hydrogen, alkyl, alkenyl, alkynyl, aryl, alkoxy, alkylthio, alkylsulfinyl, alkylsulfonyl, alkylamino, arylalkyl, or halogen;

$R^7$ is hydrogen, dialkylamino, or heteroaryl-amino;

$R^{13}$ is hydrogen, hydroxy, alkyl; alkenyl; alkynyl; alkoxy; alkylthio; alkylsulfinyl; alkylsulfonyl; alkylamino; or an arylalkyl;

Y' and Y are each independently hydrogen; halogen; hydroxyl; cyano, sulfhydryl; amino; alkyl; alkenyl; alkynyl; alkoxy; alkylthio; alkylsulfinyl; alkylsulfonyl; alkylamino; or an arylalkyl;

$R^9$ is hydrogen, or heteroaryl-amino;

and pharmaceutically acceptable salts thereof, provided that $R^9$ is not hydrogen when $R^7$ is dialkylamino or hydrogen.

46. The method of claim 45, wherein said reactive intermediate is a 7- or 9-diazonium salt.

47. The method of claim 45, wherein said reactive intermediate is a 7- or 9-nitro compound.

48. The method of claim 45, wherein said reactive intermediate is a 7- or 9-thiourea.

49. The method of claim 45, wherein said reactive intermediate is a 7- or 9-thiocarboxamide.

50. The compound of claim 1, wherein said compound is:

51. The compound of claim 1, wherein said compound is 9-(Ethylthiazolyl) amino doxycycline.

52. The compound of claim 1, wherein said compound is (4-Fluorophenylthiazolyl) amino doxycycline.

84

53. The compound of claim 1, wherein said compound is 9-(4'-Methoxyphenylthiazolyl) amino doxycycline.

54. The compound of claim 1, wherein said compound is 9-(3'-Nitrophenylthiazolyl) amino doxycycline.

55. The compound of claim 1, wherein said compound is 9-(4'-Methyl, 5'-phenylthiazolyl) amino doxycycline.

56. The compound of claim 1, wherein said compound is 9-(Phenylthiazolyl) amino sancycline.

57. The compound of claim 1, wherein said compound is 9-(Adamantylthiazolyl) amino doxycycline.

58. The compound of claim 1, wherein said compound is 9-(Phenylthiazolyl) amino minocycline.

59. The compound of claim 1, wherein said compound is 9-(Ethylthiazolyl) amino minocycline.

60. The compound of claim 1, wherein said compound is (4'-Fluorophenylthiazolyl) amino minocycline.

61. The compound of claim 1, wherein said compound is 9-(4'-Methoxyphenylthiazolyl) amino minocycline.

62. The compound of claim 1, wherein said compound is 9-(3'-Nitrophenylthiazolyl) amino minocycline.

63. The compound of claim 1, wherein said compound is 9-(4'-Methyl, 5'-phenylthiazolyl) amino doxycycline.

64. The compound of claim 1, wherein said compound is 9-(Adamantylthiazolyl) amino minocycline.

65. The compound of claim 1, wherein said compound is 7-(3'-Nitrophenylthiazolyl) amino sancycline.

66. The compound of claim 1, wherein said compound is 9-(3'-Ethoxycarbonylthiazolyl) amino doxycycline.

67. The compound of claim 1, wherein said compound is

68. The compound of claim 1, wherein said compound is:

69. The compound of claim 1, wherein said compound is:

70. The compound of claim 1, wherein said compound is:

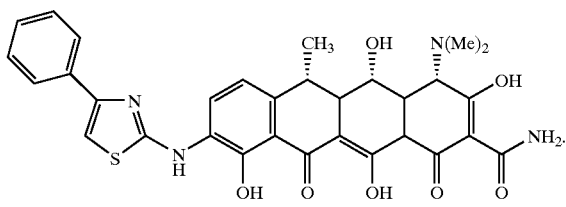

71. The compound of claim 1, wherein said compound is:

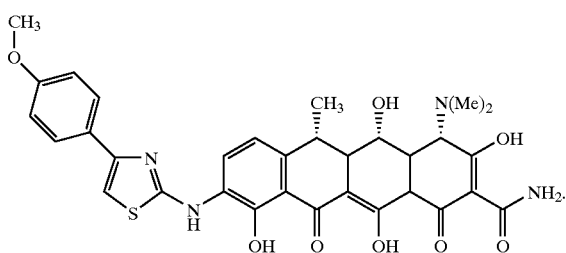

72. The compound of claim 1, wherein said compound is:

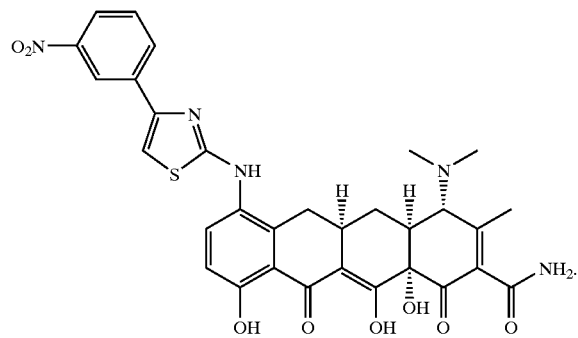

73. The compound of claim 1, wherein said compound is:

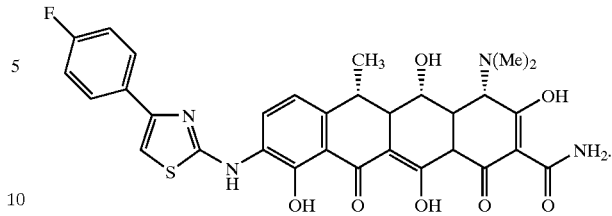

74. The compound of claim 1, wherein said compound is:

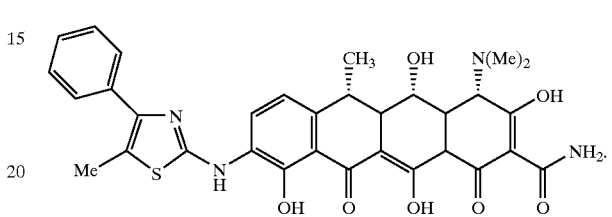

75. The compound of claim 1, wherein said compound is: 7-(Adamantylthiazolyl) amino doxycycline.

76. The compound of claim 1, wherein said compound is 7-(3-Ethylthiazolyl) amino doxycycline.

77. The compound of claim 1, wherein said compound is 7-(4"-Fluorophylthiazolyl) amino doxycycline.

78. The compound of claim 1, wherein said compound is 7-(4"-Methoxyophenylthiazolyl) amino doxycycline.

79. The compound of claim 1, wherein said compound is 7-(Phenylthiazolamino)-sancycline.

80. The compound of claim 1, wherein said compound is 7-(3"-Nitrophenylthiazolyl) amino doxycycline.

81. The compound of claim 1, wherein said compound is 7-(4"-Methyl, 5'-phenylthiazolyl) amino doxycycline.

* * * * *